(12) United States Patent
Miao et al.

(10) Patent No.: US 10,779,998 B2
(45) Date of Patent: Sep. 22, 2020

(54) ABSORBENT ARTICLE WITH CONTOURED FIT

(71) Applicant: Kimberly-Clark Worldwide, Inc., Neenah, WI (US)

(72) Inventors: Lin Miao, Beijing (CN); Xiaoling Huang, Beijing (CN); Han Chen, Beijing (CN); Chun Lei Pu, Beijing (CN); Xueen Hao, Melbourne (AU)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 267 days.

(21) Appl. No.: 15/570,094

(22) PCT Filed: May 15, 2015

(86) PCT No.: PCT/CN2015/079018
§ 371 (c)(1),
(2) Date: Oct. 27, 2017

(87) PCT Pub. No.: WO2016/183709
PCT Pub. Date: Nov. 24, 2016

(65) Prior Publication Data
US 2018/0133071 A1    May 17, 2018

(51) Int. Cl.
*A61F 13/47*    (2006.01)
*A61F 13/511*   (2006.01)
(Continued)

(52) U.S. Cl.
CPC ...... *A61F 13/51104* (2013.01); *A61F 13/539* (2013.01); *A61F 13/53747* (2013.01);
(Continued)

(58) Field of Classification Search
CPC .............. A61F 13/51104; A61F 13/539; A61F 13/53747; A61F 2013/53782;
(Continued)

(56) References Cited

U.S. PATENT DOCUMENTS 3,115,877 A   12/1963   Harwood
3,463,154 A    8/1969   Hendricks
(Continued)

FOREIGN PATENT DOCUMENTS

CN   1310989 A   9/2001
CN   1731965 A   2/2006
(Continued)

*Primary Examiner* — Peter S Vasat
*Assistant Examiner* — Meagan Ngo
(74) *Attorney, Agent, or Firm* — Kimberly-Clark Worldwide, Inc.

(57) ABSTRACT

An absorbent article includes a topsheet layer, backsheet layer, and a subjacent layer between the topsheet layer and backsheet layer. A compressible fluid management layer is positioned between the topsheet layer and subjacent layer. The compressible fluid management layer has an inner edge that defines an annular opening, with the annular opening extending entirely through the compressible fluid management layer. The compressible fluid management layer includes a dimension which is smaller than a dimension of the subjacent layer. The absorbent article further includes a first embossed feature positioned at least at portions, within the annular opening, and adjacent to the compressible fluid management layer inner edge, shaped to conform to the shape of the inner edge. The first embossed feature is positioned within the topsheet layer and the subjacent layer. The article also includes a second embossed feature positioned lateral to compressible fluid management layer peripheral edges.

32 Claims, 16 Drawing Sheets

(51) Int. Cl.
*A61F 13/537* (2006.01)
*A61F 13/539* (2006.01)
*A61F 13/475* (2006.01)

(52) U.S. Cl.
CPC ......... *A61F 13/475* (2013.01); *A61F 13/4753* (2013.01); *A61F 2013/53782* (2013.01)

(58) Field of Classification Search
CPC ........ A61F 2013/53765; A61F 13/5376; A61F 13/47236; A61F 13/475; A61F 13/494; A61F 13/4587; A61F 13/47263; A61F 13/4752; A61F 13/4753; A61F 13/4756; A61F 13/4706
See application file for complete search history.

(56) References Cited

U.S. PATENT DOCUMENTS

| | | | |
|---|---|---|---|
| 3,805,790 A | 4/1974 | Kaczmarzyk et al. | |
| 4,804,380 A | 2/1989 | Lassen et al. | |
| 5,007,906 A | 4/1991 | Osborn, III et al. | |
| 5,037,417 A | 8/1991 | Ternstroem et al. | |
| 5,401,266 A | 3/1995 | Runeman et al. | |
| 5,415,640 A * | 5/1995 | Kirby | A61F 13/512 604/383 |
| 5,514,104 A | 5/1996 | Cole et al. | |
| 5,591,150 A | 1/1997 | Olsen et al. | |
| 5,662,633 A | 9/1997 | Doak et al. | |
| 5,713,886 A | 2/1998 | Sturino | |
| 5,722,967 A | 3/1998 | Coles | |
| 5,792,129 A | 8/1998 | Johansson et al. | |
| 5,807,367 A * | 9/1998 | Dilnik | A61F 13/494 604/369 |
| 5,810,798 A | 9/1998 | Finch et al. | |
| 6,100,442 A | 8/2000 | Samuelsson et al. | |
| 6,114,597 A | 9/2000 | Romare | |
| 6,241,714 B1 | 6/2001 | Raidel et al. | |
| 6,475,203 B1 | 11/2002 | Rubio | |
| 6,524,291 B1 | 2/2003 | Bjoerklund et al. | |
| D472,313 S | 3/2003 | Leahy | |
| 6,604,609 B2 | 8/2003 | Bruce et al. | |
| D482,446 S | 11/2003 | Rainville-Lonn et al. | |
| D486,228 S | 2/2004 | Fonseca et al. | |
| 6,866,658 B2 | 3/2005 | Drevik et al. | |
| 6,932,801 B1 | 8/2005 | Samuelsson | |
| 6,974,892 B2 | 12/2005 | Decarvalho et al. | |
| 7,056,311 B2 | 6/2006 | Kinoshita et al. | |
| 7,279,613 B2 | 10/2007 | Nozaki et al. | |
| 7,335,810 B2 | 2/2008 | Yoshimasa et al. | |
| 7,530,973 B2 | 5/2009 | Tanio et al. | |
| 7,601,144 B2 | 10/2009 | Drevik | |
| 7,727,212 B2 | 6/2010 | Sakai et al. | |
| 7,857,797 B2 | 12/2010 | Kudo et al. | |
| D636,487 S | 4/2011 | Nnenna | |
| 8,187,242 B1 * | 5/2012 | Raidel | A61F 13/474 604/385.201 |
| 2003/0187418 A1 | 10/2003 | Kudo et al. | |
| 2004/0260263 A1 * | 12/2004 | Tamagawa | A61F 13/4704 604/385.04 |
| 2005/0148973 A1 * | 7/2005 | Tamura | A61F 13/15203 604/380 |
| 2005/0256472 A1 | 11/2005 | Tsutsui | |
| 2006/0206076 A1 | 9/2006 | Chiang | |
| 2007/0043330 A1 | 2/2007 | Lankhof et al. | |
| 2010/0069868 A1 | 3/2010 | Noda et al. | |
| 2010/0114049 A1 | 5/2010 | Noda et al. | |
| 2011/0319851 A1 * | 12/2011 | Kudo | A61F 13/4704 604/380 |
| 2012/0265162 A1 * | 10/2012 | Kuramochi | A61F 13/4758 604/385.101 |
| 2012/0277711 A1 * | 11/2012 | Kim | A61F 13/4756 604/374 |
| 2013/0274701 A1 * | 10/2013 | Hayashi | A61F 13/4702 604/385.101 |
| 2014/0128828 A1 * | 5/2014 | Andersson | A61F 13/53717 604/383 |

FOREIGN PATENT DOCUMENTS

| | | |
|---|---|---|
| CN | 101474112 A | 7/2009 |
| CN | 301832997 S | 2/2012 |
| CN | 102596139 A | 7/2012 |
| CN | 302458271 S | 6/2013 |
| CN | 103429201 A | 12/2013 |
| EP | 0231974 A1 | 8/1987 |
| EP | 0249405 B1 | 8/1992 |
| GB | 2354449 B2 | 3/2001 |
| GB | 2358588 B2 | 4/2004 |
| GB | 2415629 A | 1/2006 |
| JP | 10-201788 A | 8/1998 |
| JP | 4124314 B2 | 7/2008 |
| JP | 4628603 B2 | 2/2011 |
| JP | 2011-156070 A | 8/2011 |
| JP | 4976066 B2 | 7/2012 |
| JP | 5084442 B2 | 11/2012 |
| JP | 5305812 B2 | 10/2013 |
| WO | WO 1995/015139 A1 | 6/1995 |
| WO | 03103551 A1 | 12/2003 |
| WO | WO 2014/104952 A1 | 7/2014 |

* cited by examiner

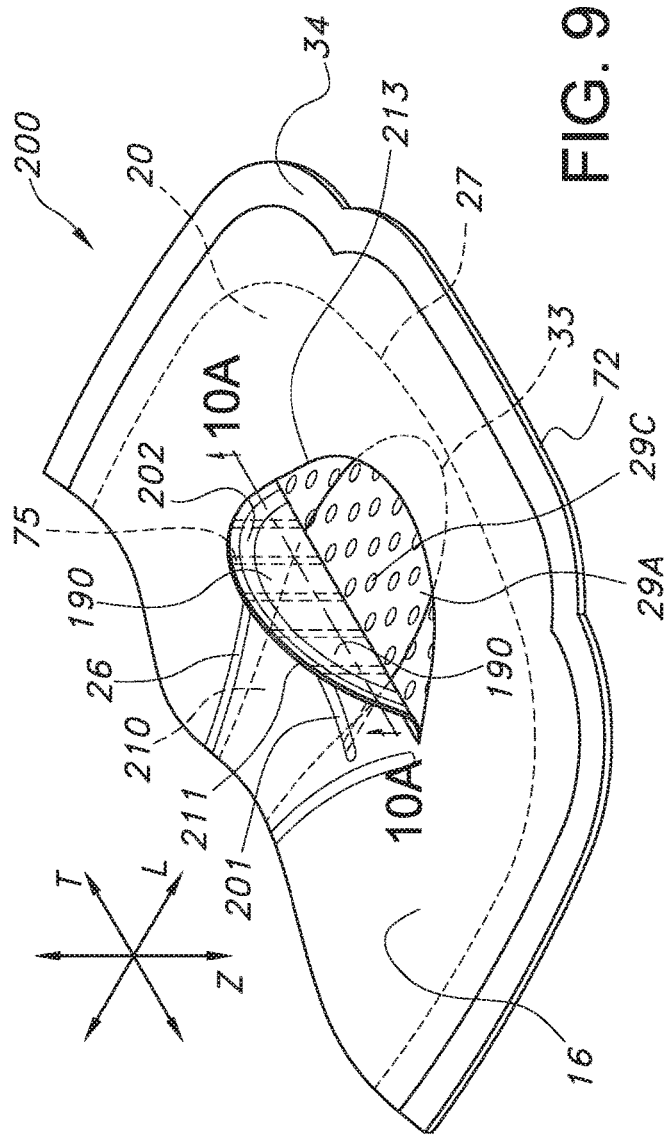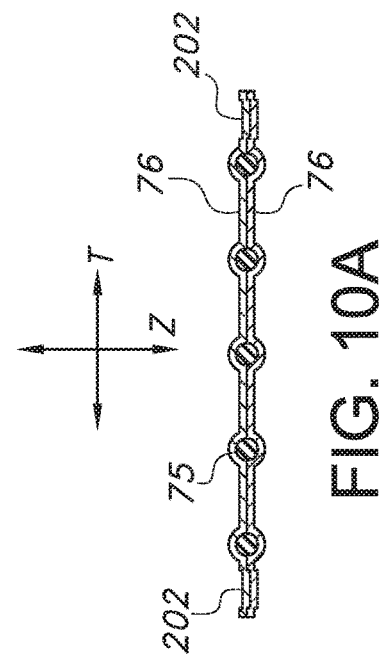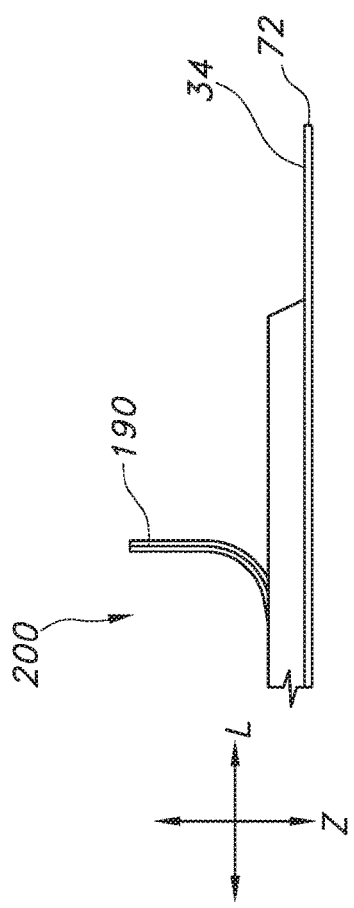
FIG. 9
FIG. 10A
FIG. 10

ABSORBENT ARTICLE WITH CONTOURED FIT

FIELD OF THE INVENTION

The present invention is generally directed to absorbent personal care articles. In particular, the present invention is directed to absorbent personal care articles with apertured fluid management layers, as well as methods for producing such articles.

BACKGROUND OF THE INVENTION

Absorbent personal care articles are often used to protect consumer undergarments and outer garments from soiling, and to collect and retain body exudates such as menses, blood, or urine. Such articles are most commonly placed in the crotch region of undergarments during use. These articles traditionally include in some form or another, a liquid permeable skin-contacting layer (also known as a topsheet layer), a liquid impermeable, undergarment-contacting layer (also known as a backsheet layer), and one or more absorbent core layers sandwiched and sealed between the topsheet and backsheet layers. These articles come in a variety of shapes and sizes depending on intended use. For example, feminine care sanitary pads are available in relatively smaller sizes to be worn during a woman's day-time activities, and extended length sizes to be worn while a woman is sleeping.

Such articles may also include additional fluid management layers positioned between the topsheet and absorbent core layers, in order to enhance fluid transport to the absorbent core layer and/or to reduce the backflow of fluid from the absorbent core layer to the topsheet layer (also known as "rewet"). Such fluid management layers may provide an elevated structure or "hump" to the article so that the area of the article that is placed immediately under that region of a wearer's body from which exudates flow, will be in constant contact with the absorbent article. Some known fluid management layers also serve to provide both an unimpeded channel for body exudate to flow directly to a subjacent absorbent core layer (or absorbent core layer system) from a topsheet layer, and also a fluid-capture, well-like structure for containing body exudate in a large open space either beneath or adjacent a topsheet layer, while excess exudate is steadily being absorbed by the absorbent core layer. These well-like structures are frequently in the form of cut-out holes in relatively planar sheets within the article.

In the context of such articles, absorbency and comfort are two main product attributes and areas of concern for the wearers of such articles. In particular, wearers are often interested in knowing that such articles will sufficiently capture and absorb large volumes of body exudates in order to protect their garments, or bedsheets from staining. Since such articles are worn adjacent a wearer's genital and buttocks regions, areas of the body that are particularly sensitive and prone to irritation, the wearers are also interested in having such articles be conformable but dry, over the multiple hours that they are usually worn.

As a result of these two consumer preferences, manufacturers have developed ultra-thin absorbent articles which include well-like features so that such absorbent articles bend and flex across most of their surfaces, while still providing a structure that contains body exudate in a confined, discrete location. For example, U.S. Pat. No. 5,810,798 to Finch et al. and international publication WO97/33546 to Raidel et al., describe the use of relatively large apertured upper layers, to direct fluid to lower absorbent core layers within an article. Such apertured upper layers channel body exudate to an absorbent core layer or core layer system via the aperture, without the exudate having to pass through an intermediate layer. Should such exudate volume be particularly sudden or large, the apertured upper layer can also maintain such exudate in its well-like structure (created by the aperture) away from the topsheet layer (depending on article design) and the wearer's skin, while the absorbent core layer gradually takes in the excess fluid. The overall absorbency rate of the article can be sped up by allowing for the deposition of body exudates directly into the absorbent layer (following passage through the topsheet) rather than through a series of intermediate layers. However, even with such apertured upper, article layer, there is still a need for apertured layers which provide for enhanced comfort/conformability, and that also provide for further fluid capture benefits for ultra-thin articles. The attributes of enhanced comfort and conformability often require a more cushion-like structure. However, cushion-like structures are usually less stable and more likely to be negatively impacted by lateral compression forces, which forces are common for absorbent articles of the types described herein. Such lack of dimensional stability leads to layer deformation, which ultimately may lead to fluid leakage. There is therefore a need for such apertured layers that demonstrate dimensional stability (and/or the ability to deform and recover) in light of the constant forces of compression on absorbent articles that result from pressure from a wearer's upper/inner thighs during use.

Several references which describe apertured upper, article layers, also have described the use of underlying printed layers to highlight the well-like structure, to enhance a user's confidence in the ability of such product to absorb large quantities of body exudate, and to assist the wearer in product placement (i.e. the aperture) beneath a particular body location. For example, international publications WO2011/053044 to Kim et al. and WO2014/085974 to Miao Lin et al., describe the use of printed layers beneath a relatively large aperture. While such layers are effective in highlighting such aperture feature, there is still a need for articles which further define such well-like features so as to instill further consumer confidence in the absorbency attributes of an article, and to further assist consumers in product placement. There is a further need to create a more pronounced cushion-like layer to provide additional comfort to a wearer and to maintain a close association of the article against the wearer's body, without compromising the dimensional stability of the cushion-like layer.

Several references also describe use of surrounding embossing channels to limit lateral flow of body exudate off article lateral-most side edges, beyond an apertured layer peripheral side edges. For example, international publications WO2011/053044 to Kim et al. and WO2014/085974 to Miao Lin et al., describe the use in articles of apertured layers (i.e. layers having relatively large annular openings) in conjunction with embossed features of other layers, which embossed features are positioned laterally outward from the peripheral side edges of the apertured layer. However, such apertured layers do not take advantage of embossment features of other layers in order to enhance the comfort function of the apertured layer, or to further define the aperture itself. While international publication WO09/067059 to Gustin Bergstrom et al., describes the use of embossed features within the material of an upper apertured layer itself, such embossment is described as being designed to enhance the flexibility/fold indications of the upper apertured layer. Further, European patent publication EP0343941 to Reising describes the use of a bonding mechanism such as adhesive or ultrasonic means, to attach a layer located above an aperture to a layer located beneath an aperture, and through the aperture itself. However such reference illustrates a transversely spaced apart bonding mechanism across the full width of the aperture opening, and does not use such bonding to further define the aperture feature itself. Therefore, there is still a need for such apertured layers which utilize separate embossed features within other, non-apertured layers so as to enhance a wearer's comfort, to further define a large aperture, and to also provide an enhanced fluid capture region within the aperture itself.

As noted previously, manufacturers of absorbent articles have developed increased length, and asymmetrically-shaped pads to assist consumers in managing the release of body fluids over extended time frames, such as throughout the night. Many of such articles include elevated areas located along the article longitudinal centerline and towards the back region of the article in order to improve fluid capture while the consumers are in a side or supine sleeping position. Such raised areas are designed to be placed within the intergluteal cleft and adjacent the buttocks of a wearer. Such elevated structure is exemplified by U.S. Pat. No. 7,335,810 to Yoshimasa et al. As seen in Yoshimasa, such elongated hump-like structures are frequently shown as being closely surrounded by a compressed groove or grooves. However, despite some success of elongated hump-like features in catching fluid that might seep onto a pad during a night, and the presence of surrounding, embossed features with such humps, there is still a need for overnight pad articles which provide for enhanced leakage control and product fit in conjunction with the hump(s).

WO2014/085974 to Miao Lin et al. describes the use of encircling-type, dual-cover layer structures to help target fluid to subjacent core layers and to provide comfort benefits to an article. However, such reference does not contemplate the use of coordinated embossment features with such dual-covers in order to enhance aspects of an aperture structure.

Concentric embossed features are also known in the absorbent article field, such as for example those shown in European Patent No. EP1306069B2 to Wada. However, such concentric embossed features are not described as enhancing a fluid-capture, well-like structure within an absorbent article. There is therefore a need for articles with well-like structures using embossments that enhance the performance of the well-like structures.

While cushioned, ring-like structures are described in the absorbent article patent literature for providing comfort to a user of such articles, they do not take advantage of embossment features for enhanced comfort, stability, and fluid capture benefits within the aperture itself. For example, raised circumferential banks and saddle structures are described for use in absorbent articles in international publication WO03/053314A to Ohshima et al. While such structures are described as being compressible resilient structures, with certain degrees of recovery, such structures are not described as being used with embossment features of other layers in order to enhance comfort, stability, or fluid capture functionality of the apertured layer itself, or of overnight pad products. There is therefore a need for absorbent articles including overnight pad products, with upper, apertured layers having dimensionally stable structures which utilize multiple features to enhance the comfort and fluid capture abilities of the upper apertured layers.

SUMMARY OF THE INVENTION

In one embodiment, an absorbent article has a longitudinal direction, a transverse direction, and a depth direction and includes a topsheet layer, a backsheet layer, an absorbent layer between the topsheet layer and the backsheet layer, and a compressible fluid management layer between the topsheet layer and the absorbent layer, with each of the topsheet, backsheet, absorbent, and compressible fluid management layers having respective longitudinal direction, transverse direction and depth direction dimensions. The longitudinal and transverse direction dimensions are defined by longitudinal direction end edges and transverse direction side edges respectively. The compressible fluid management layer has an inner edge that defines an annular opening, with the annular opening extending entirely through the compressible fluid management layer depth direction dimension. The compressible fluid management layer includes a transverse dimension which is smaller than the transverse dimension of the absorbent layer.

The absorbent article further includes a first embossed feature positioned at least at portions, within the annular opening, and adjacent to the compressible fluid management layer inner edge. The first embossed feature is positioned within the topsheet layer and the absorbent layer. The absorbent article further includes a second embossed feature configured at least at portions, lateral to at least the compressible fluid management layer transverse direction side edges and positioned within the topsheet layer and the absorbent layer.

In an alternative embodiment the compressible fluid management layer extends a length along the majority of the longitudinal direction of the absorbent layer. In a further alternative embodiment, the compressible fluid management layer includes at least one flared longitudinal direction end. In yet another alternative embodiment, at least a portion of the first embossed feature is positioned a lateral distance from the inner edge by between about 0.5 mm and 10 mm, alternatively between about 1.0 and 5 mm, alternatively between about 1 and 3 mm. In still a further alternative embodiment, the entirety of the first embossed feature is positioned within the annular opening.

In still another alternative embodiment, the first embossed feature is selected from the group consisting of a continuous embossed channel and a discontinuous series of discrete embossed shapes, wherein the inner edge has an overall shape, and further wherein the first embossed feature is configured to be of the same shape as the inner edge overall shape. In another alternative embodiment, at least a portion of the second embossed feature is positioned laterally outward from the compressible fluid management layer transverse direction side edges by a distance of between about 0.5 mm and 200 mm, alternatively between about 1 mm and 100 mm, alternatively between about 1 mm and 20 mm.

In still another embodiment, the entirety of the second embossed feature is positioned laterally outward from the compressible fluid management layer transverse direction side edges and longitudinal direction end edges. In still another embodiment, the second embossed feature is selected from the group consisting of a continuous embossed channel and a discontinuous series of discrete embossments. In yet another embodiment, the compressible fluid management layer transverse direction dimension includes non-straight side edge portions along the article longitudinal direction.

In another embodiment, the compressible fluid management layer includes a first, forward-directed region having a forward-directed region length, and having a maximum transverse dimension width, a second middle region which includes the annular opening, and an elongated rearward-directed region of a length longer than the forward-directed region length, and having a transverse dimension width which is narrower than the first, forward-directed region maximum transverse width.

In another embodiment, the second embossed feature includes outwardly flared end elements, which are flared away from (and away from the central longitudinal direction of the article) the compressible fluid management layer, transverse dimension side edges. In another embodiment the inner edge defining the annular opening has a shape, and the first embossed feature is of the same overall shape as said inner edge, such as an oval or elliptical shape. In another embodiment, the second embossed feature is discontinuous and includes at least two separated ends, and the compressible fluid management layer extends beyond the at least separated ends of the second embossed feature along the article longitudinal direction.

In still another embodiment, the absorbent article includes a vaginal placement zone, a gluteal cleft transition zone, for placement adjacent the intergluteal cleft, and a coccyx zone, and further wherein the compressible fluid management layer has a length that extends into said coccyx zone. In another embodiment, the compressible fluid management layer includes relatively smaller discrete apertures through the entire thickness of the layer, in addition to the relatively larger annular opening.

In another embodiment, the first and second embossed features are shaped to align with the compressible fluid management layer inner edge and transverse dimension side edge respectively. In still another embodiment, the compressible fluid management layer is formed from a laminate of at least two layers. In another embodiment, the compressible fluid management layer includes a thickness in the depth direction of between about 1 and 20 mm, alternatively between about 1.5 and 10 mm, alternatively of between about 2 and 5 mm.

In yet another embodiment, the topsheet layer is a dual-cover topsheet layer, having a first skin exposed topsheet layer material surrounded about all its side edges by a second skin exposed topsheet layer material, and further wherein the first skin exposed topsheet layer material includes skin exposed longitudinal and transverse edge dimensions larger than the longitudinal and transverse dimensions of the compressible fluid management layer. In another embodiment, the topsheet layer is a dual-cover topsheet layer having a first skin-exposed topsheet layer material surrounded about all its skin-exposed side edges by a second skin-exposed topsheet layer material, and further wherein the skin-exposed topsheet layer includes exposed longitudinal and transverse edge dimensions smaller than the inner edge of the annular opening.

In still a further alternative embodiment, an absorbent article has a longitudinal direction, a transverse direction, and a depth direction including a topsheet layer, a backsheet layer, at least one subjacent layer between the topsheet layer and the backsheet layer, and a compressible fluid management layer between the topsheet layer and the at least one subjacent layer, with each of the topsheet, backsheet, at least one subjacent layer, and compressible fluid management layers having respective longitudinal direction, transverse direction and depth direction dimensions, with the longitudinal and transverse direction dimensions defined by longitudinal direction end edges and transverse direction side edges respectively.

The compressible fluid management layer has an inner edge that defines an annular opening, with the annular opening extending entirely through the compressible fluid management layer depth direction dimension. The compressible fluid management layer includes a transverse dimension which is smaller than the transverse dimension of the at least one subjacent layer.

The absorbent article further includes a first embossed feature positioned at least at portions, within the annular opening, and adjacent to the compressible fluid management layer inner edge. The first embossed feature is positioned within the topsheet layer and the at least one subjacent layer. The absorbent article further includes a second embossed feature configured at least at portions, lateral to at least the compressible fluid management layer transverse direction side edges and positioned within the topsheet layer and the at least one subjacent layer.

In a further alternative embodiment, the inner edge has an overall shape, and the first embossed feature is positioned entirely within the annular opening and has an overall shape that is the same overall shape as that of the inner edge. In another embodiment, the second embossed feature is positioned laterally outward from, but adjacent to the transverse direction side edges and longitudinal direction end edges of the compressible fluid management layer.

In still another embodiment, the absorbent article includes two longitudinal ends along the longitudinal direction, and the compressible fluid management layer is of a length that extends along a substantial portion, such as greater than 50 percent, alternatively, greater than 75 percent of the longitudinal direction of the absorbent article, and further wherein the second embossed feature includes two separated, and outwardly flared ends at one longitudinal end of the absorbent article.

In yet another embodiment, an absorbent article has a longitudinal direction, a transverse direction, and a depth direction including a topsheet layer, a backsheet layer, at least one subjacent layer between the topsheet layer and the backsheet layer, and a compressible fluid management layer between the topsheet layer and the at least one subjacent layer, with each of the topsheet, backsheet, at least one subjacent, and compressible fluid management layers having respective longitudinal direction, transverse direction and depth direction dimensions. The longitudinal and transverse direction dimensions of the compressible fluid management layer are defined by longitudinal direction end edges and transverse direction side edges respectively.

The compressible fluid management layer has an inner edge of an inner edge shape, that defines an annular opening, with the annular opening extending entirely through the compressible fluid management layer depth direction dimension. The compressible fluid management layer includes a transverse dimension which is smaller than the transverse dimension of the at least one subjacent layer.

The absorbent article further includes a first stabilizing element positioned at least at portions, within the annular opening, and adjacent to the compressible fluid management layer inner edge, with the first stabilizing element positioned within the topsheet layer and the at least one subjacent layer and having the same shape as the inner edge shape.

A second stabilizing element is also present in the absorbent article, that is configured at least at portions, lateral to at least the compressible fluid management layer transverse direction side edges and positioned within the topsheet layer and the at least one subjacent layer.

BRIEF DESCRIPTION OF THE DRAWINGS

A full and enabling disclosure of the present invention is set forth more particularly in the remainder of the specification, including reference to the accompanying figures, in which:

FIG. 9 illustrates an enlarged partial perspective view of one end of the overnight sanitary pad of FIG. 7 with a back flap elevated.

FIG. 10 illustrates an enlarged partial side view of the end of the overnight sanitary pad illustrated in FIG. 9 with a back flap elevated.

FIG. 10A illustrates a cross sectional view along line 10A-10A of the back flap feature illustrated in FIGS. 9 and 10.

DEFINITIONS

Figure 1:
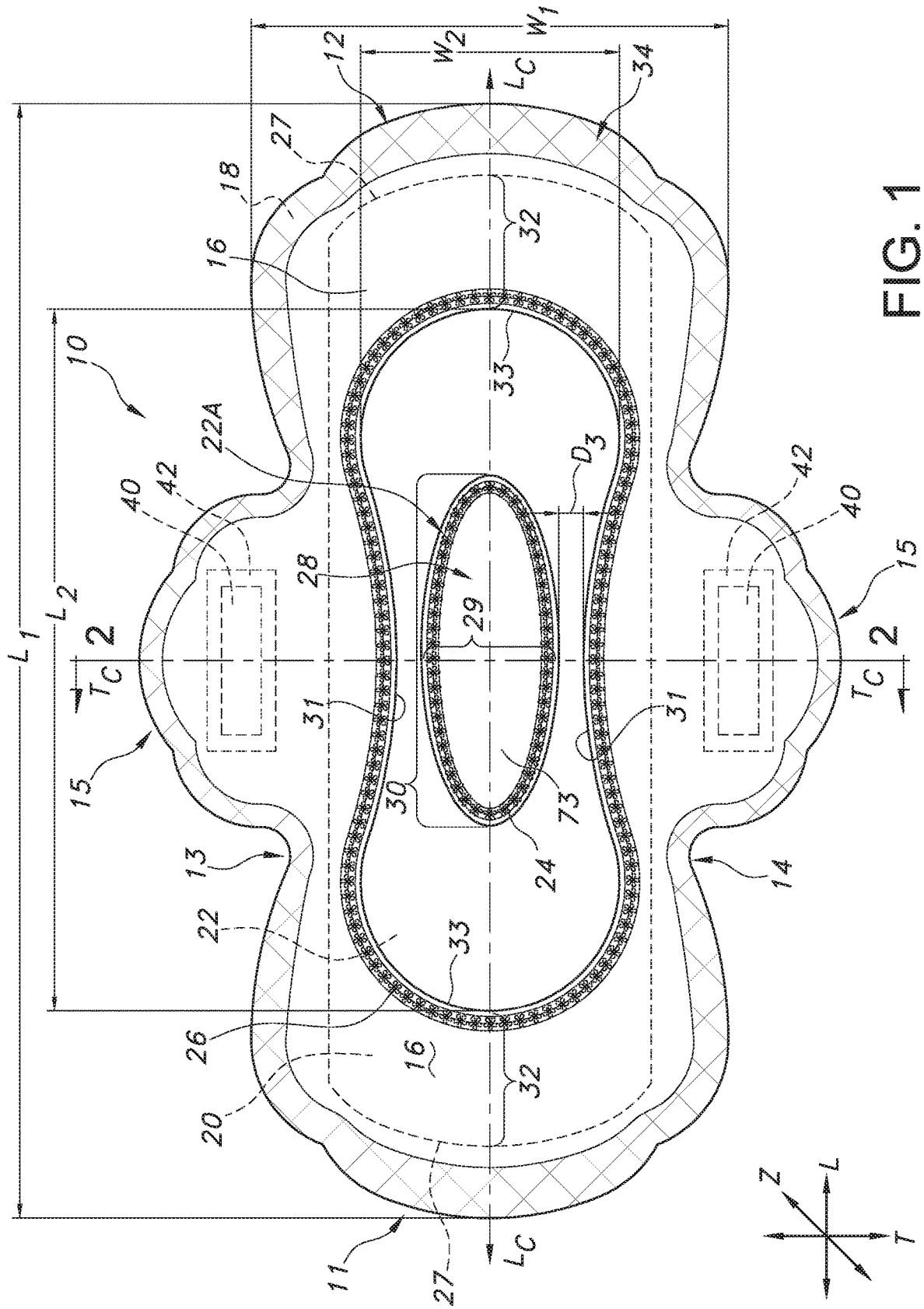
FIG. 1 illustrates a top plan view of a feminine care absorbent personal care article in accordance with the invention, specifically in the form of a sanitary pad.

As used herein, the term "compressible" shall refer to the ability of a layer to be compacted in its thickness direction, such that upon compaction, its thickness dimension is reduced. Upon removal of a compaction force, the compressible layer will recover at least some of its original dimension in the thickness direction. In a desirable embodiment, a compressible layer shall be a resilient or elastic layer, having a "starting" layer thickness, to be compacted upon application of compaction pressure/force when the sample layer is in a dry and unsoiled condition, such that the layer starting thickness is reduced (in at least one location along its length or width dimension) during compaction to create a "compacted" layer thickness, following initial removal of the compaction pressure/force. Upon removal of the compaction pressure/force, and over a given time period of relaxation, the layer will recover at least some of its thickness to result in a "final" thickness.

Desirably, in one embodiment, such compressible layer is compressible by at least 5% of its starting thickness, more desirably by at least 10%, even more desirably by at least 25%. Desirably, in one embodiment, such final thickness, which is measured after 30 minutes of removal of the compaction pressure, is approximately the same thickness dimension as the starting thickness. Alternatively, such final thickness is desirably within 25% of the starting thickness. Alternatively, such compressible layer is capable of recovering at least some of its starting thickness following removal of the compaction pressure, desirably in one embodiment, to a final thickness of at least 70% of its starting thickness. Alternatively, such compacted layer is capable of recovering to at least 50% of its starting thickness. For example, if a starting sample layer of 5.0 mm in thickness is compacted to 2.0 mm (thereby having a compaction of 3.0 mm), it is desirable that such layer return to approximately its original 5.0 mm (as final thickness) upon removal of the compaction pressure and the passage of a limited period of time. Alternatively, for at least 70% of its starting thickness, such layer will recover 1.5 mm of its total compaction (3.0 mm) such that its final thickness following removal of the compaction pressure (and over the lapse of a stated time) is 3.5 mm. In an alternative, for at least 50% of its starting thickness, such layer will recover 0.5 mm of its total compaction (3.0 mm) such that its final thickness following removal of the compaction pressure/force (and over the lapse of a stated time period) is 2.5 mm.

Desirably, for the purpose of a resiliency/compressibility measurement for this attribute, a 700 g metal block is applied (sole pressure is of the block on a material) for 120 minutes, when the article or layer is in a dry and unsoiled state and in a generally flat/unwrinkled condition. The suggested metal block dimensions are of 120 mm by 80 mm by 26 mm with the widest block dimension facing the flat sample material.

The article or layer sample is first measured for its initial thickness prior to compression, immediately following compression and removal of the compaction pressure/force, and after at least 30 minutes following removal of the compaction pressure/force. In particular, following removal of the pressure, the sample of the individual layer (or alternatively the article as a whole) is allowed to relax for 30 minutes, with traditional manual or digital caliper measurements taken at each time frame noted above.

Specifically, in the recommended testing procedure for measuring the thickness of the sample, the thickness value of a selected sample may be determined using a thickness tester which includes a granite base having a vertical clamp shaft extending from the top surface of the granite base which is flat and smooth. A suitable granite base is a Starret Granite Base, model 653G (available from The L.S. Starrett Company, having a place of business located in Athol, Mass., U.S.A.) or equivalent. A clamp arm is secured to the clamp shaft at one end of the clamp arm, and a digital indicator is secured to the clamp arm at the opposing end. A suitable indicator is a Mitutoyo ID-H Series 543 Digimatic Indicator (available from Mitutoyo America Corp., having a place of business located in Aurora, Ill., U.S.A.) or equivalent. Extending downward from the indicator is a vertically-movable plunger.

To perform the procedure, a 119 g acrylic block (with a 0.06 psi) having the dimensions of 44 mm by 127 mm is placed onto the granite base. The block is flat and smooth on at least the bottom surface. The thickness and weight of the block is configured such that the thickness tester provides a pressure to the sample of 0.02 kPa (0.029 psi). Next, the thickness tester is gently lowered such that the bottom surface of the plunger is in direct contact with the top surface of the block at the longitudinal and transverse center of the block, and the plunger length is shortened by about 50%. The digital indicator is then tared (or zeroed) by pressing the "zero" button. The digital display of the digital indicator should display "0.00 mm" or equivalent. The thickness tester is then raised and the block is removed. The test sample is then placed onto the top surface of the granite base and the block is gently placed on top of the flat test sample such that the block is substantially centered longitudinally and transversely on the sample. The thickness tester is then gently lowered again onto the block such that the bottom surface of the plunger is in direct contact with the top surface of the block at the longitudinal and transverse center of the block, and the plunger length is shortened by about 50%, to provide a pressure of 0.02 kPa (0.029 psi). After 3 seconds, the measurement from the digital display is recorded to the nearest 0.01 mm. Measurements are taken of the sample initially, and then of the sample after two hours (the metal block has been situated on the sample for two hours and then removed), and then within 30 minutes following block removal.

To prepare the samples for thickness measurement, the samples may be measured and cut to a dimension of 34 by 150 mm with the long dimension in the machine direction. The testing should be accomplished under ambient conditions. The samples should be placed on the tester body side facing up, as flat as possible, and wrinkle free.

As used herein, the term "fluid management" shall refer to a layer within an absorbent article which can assist in the channeling or directing of body exudate to a layer beneath it from a layer above it, without presenting any physical obstruction to body exudate flow passing through an aperture or annular opening defined by such layer. In other words, such fluid management layer shall define an aperture or annular opening which allows for the direct and non-circuitous movement of fluid from the layer above it (through the aperture) to a layer beneath it.

As used herein, the term "stabilizing element" shall refer to a reinforcing structure within an absorbent article that lends lateral support to a layer by anchoring or connecting other layers adjacent and subjacent to the layer that is to be supported. An example of a stabilizing element may include an embossed feature, a bond, or other connecting feature between two or more layers.

As used herein, the term "embossed feature" shall refer to a depressed feature within the absorbent article which is formed between at least two layers of the article, and which is created by pressure (and in alternative embodiments, additionally with either thermal and/or ultrasonic bonding techniques as well). Desirably, such embossing bonds or joins at least two layers together within the absorbent article, but can join as many as seven (7) or more layers together in the Z direction. Traditionally, such embossing process compacts the at least two layers during the process of manufacture, such that the density of the material in the compacted areas is of a higher amount than surrounding, not compacted regions. For the purposes of this disclosure, an embossed feature may be either a continuous channel, a series of discrete dots, dashes, or shapes, or a combination of the two. Such shapes may include geometric shapes such as circles, triangles, or squares, or alternatively, abstract shapes, or alternatively, shapes from nature such as stars or flowers. Such embossed features may alternatively be comprised of a combination of shapes. Such embossed features may be comprised of macro-embossments, that is larger shapes, and if desired, micro-embossments, that is patterns within macro-embossments. Examples of micro-embossments and macro-embossments are described in Korean Patent KR 101198546B1 to Hwang et al., which is incorporated by reference hereto in its entirety. Embossed features may be typically created by embossing rolls and embossing plates.

Desirably, embossed features have a depth within an article of between about 0.1 mm and 4.0 mm, alternatively between about 0.2 mm and 2.0 mm, as measured from the bottom inside surface of such embossed feature to the upper top edge of such embossed feature (the level of the unembossed material surrounding the embossed feature). Desirably, such embossed features have a width across their narrowest dimension of greater than 0 mm (such as 0.1 mm) to about 30 mm, alternatively between about 1 mm and about 15 mm, alternatively, between about 5 mm and 15 mm. An example of a method and type of embossed feature is described in U.S. Pat. No. 5,795,344 to Chappell, which is hereby incorporated by reference thereto in its entirety. Other techniques for creating embossed features are well known in the art and will not further be described herein.

As used herein, the term "wearer-facing surface" shall refer to the surface of a layer within an absorbent article (i.e. sanitary pad) or of the article itself that normally faces a wearer's body in article use. Such term is distinguished from the term "skin-contacting" surface, which describes the actual surface of a layer that will make contact with the skin of a wearer when the article is being used. The wearer-facing surface is not necessarily the skin-contacting surface. The term "garment-facing surface" shall refer to the surface of a layer within an absorbent article or of the article itself, that normally faces a wearer's undergarments in article use.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, hydroentangling, and bonded carded web processes (such as thermal bonded carded webs, or TBCW and through-air bonded carded webs, or TABCW).

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Butin, et al., which is incorporated herein in its entirety by reference thereto. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto. Spunbond fibers are generally not tacky when they are deposited onto a collecting surface. Spunbond fibers may sometimes have diameters less than about 40 microns, such as between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 5,284,703 to Everhart, et al., and U.S. Pat. No. 5,350,624 to Georger, et al., each of which are incorporated herein in their entirety by reference thereto.

As used herein, the term "liquid permeable" shall refer to a material which is porous and which is water permeable due to the flow of water and other aqueous liquid or fluid through the pores of the material. The pores are large enough and frequent enough to permit leakage and flow of liquid water. "Liquid impermeable" shall refer to a material that does not allow water or aqueous liquid/fluid to pass through it under ordinary use conditions.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For example, perforations that are described for use in a compressible fluid management layer of one embodiment, and that are present in addition to the annular opening of one embodiment, may similarly be present in a compressible fluid management layer of a different embodiment.

For the purposes of this application, like features may be represented by like numbers between the figures. While not illustrated in most figures except where additional placement emphasis is desired, it should be understood that traditional article construction adhesive (or other bonding technology) is to be used to fasten the various layers of the described articles together. Such construction adhesive or other bonding technology is desirably placed or practiced so as not to interfere with the flow of body exudate through the article. Other construction bonding techniques that are contemplated include for example, ultrasonic, pressure, and thermal bonding. Traditional pressure sensitive garment-attachment adhesive and hook and loop technology is also contemplated for use with the articles for maintaining them in place in an undergarment, where noted.

The absorbent personal care articles of the present invention utilize a combination of both compressible fluid management layer attributes and embossed features, in order to create a dimensionally stable structure. The combination provides for a cushion-like layer with a stabilizing element that controls layer deformation, ultimately leading to a reduction in fluid leakage. By registering the stabilizing element (the embossing features from other layers) with the cushion-like compressible layer, the resulting apertured article demonstrates enhanced fluid capture abilities, enhanced visual prominence of fluid capture features for ease of identification by consumers and subsequent article placement, and increased consumer confidence. Additionally, the combination of features provides for enhanced comfort for a wearer.

By placement of an embossed feature laterally adjacent both opposing transverse side edges of a compressible fluid management layer, as well as adjacent to substantially the entire inner edge of an annular opening defined by the compressible fluid management layer, a highly defined, fluid capture, well-like structure is created. Such embossed features serve as stabilizing elements that provide lateral support to the compressible fluid management layer. Such support helps to prevent deformation of the compressible fluid management layer, by anchoring the layer to adjacent and subjacent layers, such as the topsheet, surge and absorbent layers. An issue that is common with traditional higher loft, cushion-like materials is deformation from lateral compression during product use. Such issue is reduced with such anchoring features. Such highly defined structure creates a cushion-like feature for targeted placement under a wearer's anatomy. In such an article, rather than having the topsheet layer elevated above the floor of the fluid-capture, well-like structure (i.e. in a level configuration across the transverse direction of the annular opening layer upper surface, from which the well-like structure is created) a topsheet layer is instead embossed with one or more layers subjacent the compressible fluid management layer, at the floor of the well-like structure, such that the layers are held together. The resulting dimensionally stable well-like structure easily funnels fluid directly to the absorbent layers with less opportunity for layer deformation. One embossed feature is positioned adjacent to, and inward from the compressible fluid management layer inner edge (which edge defines an annular opening). The embossed feature contained partially within, substantially within, or entirely within the annular opening, itself defines an enclosed or substantially enclosed area along a topsheet layer, which is substantially surrounded by the embossed feature. The embossed feature is desirably registered with the apertured layer inner edge that forms the annular opening. A second embossed feature is positioned outward from the peripheral edge of the apertured layer along at least the transverse side edges of the layer. By matching an absorbent layer system with such an apertured upper layer and embossed features, an effective and comfortable fluid capture, well-like structure is achieved.

In an alternative, by use of an encircling-type, dual-cover topsheet layer in conjunction with such a compressible fluid management layer, a variety of topsheet layer materials may be placed in an article for enhanced wearer comfort, including reduction in rewet sensations within the area of an annular opening. Use of an encircling-type, dual-cover feature further enhances visual prominence of the well-like feature of the article.

The combination of features creates an absorbent article with prominent contours on the skin-contacting surface of the article. By the inclusion of an apertured, extended length compressible fluid management layer with the embossed features, an overnight pad product with enhanced fit properties is also created that provides absorption and fluid capture benefits.

The absorbent personal care articles of the present invention are ideally suitable for use as hygiene articles in the feminine and adult care product categories. Such articles include for example, feminine sanitary pads and liners, and adult care garment inserts, pads, and liners. For the purposes of simplicity only, feminine care hygiene absorbent articles are illustrated, and in particular, feminine care day, and overnight size sanitary pads 10.

Such sanitary pads 10 include a longitudinal direction L, a transverse direction T, and a depth (or thickness) direction Z. While all illustrated articles include a central longitudinal direction Lc, some illustrated articles also include a central transverse direction Tc, such as the article 10 shown in FIG. 1. Overnight feminine hygiene sanitary pad products 100, 200 (i.e. those that are specifically designed for extended use in overnight time frames while a wearer is in a supine or side position) such as those pads shown in FIGS. 5 and 7, do not always include a central transverse direction. Such pads are frequently asymmetrical along the transverse direction.

The sanitary pad 10 of FIG. 1 includes a first longitudinal end 11, and an opposing second longitudinal end 12. Two opposing article lateral side edges 13, 14 extend along the article longitudinal direction between the longitudinal ends 11, 12. In some contemplated embodiments, optional opposing lateral extensions 15 in the forms of wings or tabs, extend outwardly from the opposing lateral side edges 13, 14 of the pad 10. While the articles are illustrated having a peripheral edge with slightly scalloped features, it should be appreciated that a variety of pad shapes are contemplated. The sanitary pad 10 includes a length L1 and a width W1. Desirably, the length L1 of the sanitary pad of the invention is between about 50 mm and 1,000 mm, alternatively between about 100 mm and 600 mm, alternatively between about 150 mm and 450 mm. Desirably, the width W1 of the sanitary pad of the invention is between about 5 mm and 1,000 mm, alternatively between about 10 mm and 300 mm, alternatively between about 20 mm and 160 mm. The width is the widest measurement of the pad along the transverse direction, excluding the width of the separate wing structures 15, as such wing structures are considered an optional feature.

All of such articles include at least one wearer-facing, skin-contacting surface in the form of a topsheet layer 16, made up of at least one liquid permeable material. A single material topsheet layer 16 is illustrated for instance, in FIG. 1. In some embodiments, such as the embodiment illustrated in FIG. 3, multiple topsheet layers may be used across the skin-contacting surface of the article 10. For instance, a liquid permeable first topsheet layer 16 (as a central longitudinally directed topsheet layer) may be used in combination with at least a second liquid permeable topsheet layer 17 or side cover, (as illustrated positioned along the opposing, article lateral side edges 13, 14), such that both topsheet layers 16, 17 have wearer-facing surfaces that are both exposed to the skin of a wearer during normal product use. Such multiple layer, topsheet configurations will be referred to as side-by-side, dual-cover topsheet layers. Often in side-by-side, dual cover topsheet layers, the side covers 17 extend out over the wings. Such layers are often used to provide soft, skin contacting regions on the pad for contacting the natural crease areas between a user's upper inner thighs and crotch (and at the crotch edges of a user's panty).

Figure 3:
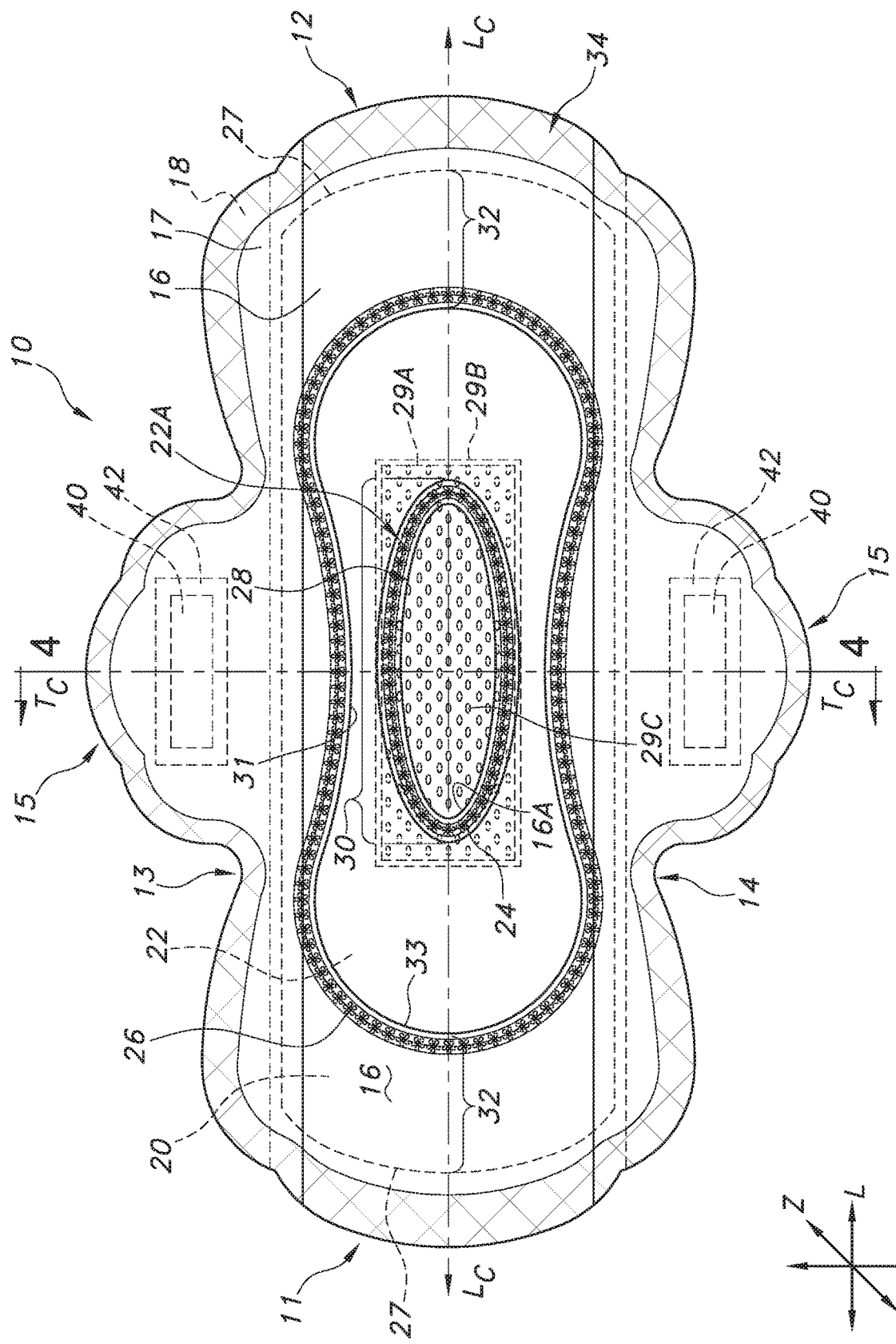
FIG. 3 illustrates a top plan view of an embodiment of a sanitary pad in accordance with the invention.

In further instances, the liquid permeable topsheet layer 16 may surround a portion of another skin-contacting liquid permeable topsheet layer 29A, as shown in FIG. 3. In this configuration, a surrounding topsheet layer 16 includes a topsheet layer inner edge 16A, which defines a central opening in the topsheet layer 16. In such an embodiment, both the surrounding topsheet layer 16 and surrounded topsheet layer 29A will include portions that are exposed to the skin of a wearer in use. The surrounded topsheet layer 29A (or central layer) is exposed to the skin through the central opening. Such dual-cover topsheet layer configuration will be referred to as an encircling, dual-cover topsheet layer. Such surrounded topsheet layer 29A may extend only partially above or below the side edges of the surrounding topsheet layer 16 (as shown in FIG. 3) in the Z direction, or may alternatively, extend along a significant portion of a garment-facing surface of the surrounding topsheet layer 16, such as to the longitudinal ends 11, 12 of the pad 10. For the purposes of this invention, an absorbent article (sanitary pad 10) is contemplated as having either a single material topsheet layer, a side-by-side, dual-cover topsheet layer, an encircling, dual-cover topsheet layer, or a combination of the two dual-cover topsheet layer configurations. A side-by-side, dual-cover topsheet layer is further described in U.S. Pat. No. 5,961,505 to Coe, U.S. Pat. No. 5,415,640 to Kirby and U.S. Pat. No. 6,117,523 to Sugahara, each of which are hereby incorporated by reference thereto in its entirety. An encircling, dual-cover topsheet layer is further described in international publication WO2014/085974 to Miao Lin et al., which is hereby incorporated by reference thereto in its entirety. As noted, in alternative embodiments a topsheet layer may include three different skin-exposed materials/layers, such as those 16, 17, and 29A illustrated in FIG. 3, or alternatively, still more numerous, skin-exposed layers such as in FIG. 3B at 16, 17, 29A, 29B. Each of such topsheet layer materials include surfaces that are exposed to a wearer's skin during product use.

Such dual-cover topsheets may place the lateral, cover layers 17 (if present) either over or under a central, longitudinally directed topsheet layer 16 (FIG. 3). Similarly, an encircling configuration, dual-cover topsheet layer may place a surrounding topsheet layer 16 either over, or under a centrally disposed topsheet layer 29A (surrounded layer) (FIG. 3). The multiple layer topsheets may be bonded to one another along their overlapping side edges, such as by adhesive, thermal, or ultrasonic bonds. The use of dual-cover topsheet layers allows for the targeted placement of specific materials at certain regions of a sanitary pad 10, for improved comfort and visual emphasis of pad structures.

Referring again to FIG. 1, the sanitary pad 10 also includes a liquid impermeable backsheet layer 18, designed to directly contact the garment or undergarment of a wearer, and which is bonded to the one or more topsheet material layers at least along the article peripheral edges in a peripheral seal region 34. Such peripheral seal region 34 desirably extends along the entire peripheral edge of the pad 10. As noted, such bonded topsheet layer(s) 16 and backsheet layer 18 often include bonded lateral extensions which together comprise the wings 15. Such bonded lateral extensions 15 frequently do not include any other layer between them at the areas of the extension 15.

On the garment-facing surface of the backsheet layer 18, fastening materials, such as adhesive patches 40 are positioned to assist the wearer in fastening wings of the pad 10 either to one another or to the wearer's undergarments when in use. As illustrated, fastening materials may include one or more central fastening strips along the central longitudinal direction Lc of the pad, and two wing fastening strips on the garment facing surfaces of the wings 15. It should be recognized that such fastening materials may include adhesives, hook and loop-type fasteners, or a combination of the two, as are well-known in the art. If such fastening materials are adhesive, release sheets 42 may also be used to protect the adhesive patches 40 until actual use.

At least one absorbent layer 20 (20C-20D in certain embodiments) is held between the topsheet layer(s) 16 and the backsheet layer 18 within the main body of the sanitary pad (as opposed to the wings). As illustrated, the absorbent layer 20 may itself include multiple layers, such as a functional variety of absorbent layers. Alternatively, the absorbent layer may be part of an absorbent system including primary fluid storage layers and fluid pass-through layers (which are not designed to retain fluid). As an example, such layers may include a primary storage layer designed to retain absorbed body exudate, and liquid pass-through layers, such as fluid distribution layers, or surge layers.

The absorbent layer(s) 20 in one embodiment, desirably extend substantially along the longitudinal direction L and transverse direction T of the sanitary pad 10, but is slightly shorter than the full length L1 and full width W1 and contained between the peripheral seal region 34 of the article, so as to avoid leakage of fluid from the sanitary pad 10 at the seal region 34. The absorbent core layer 20 may be present in any of a variety of shapes, such as for example, rectangular, oval, or dogbone configurations.

A compressible fluid management layer 22 is positioned subjacent the topsheet layer(s) 16, and desirably above at least one surge 20A, 20B and absorbent layer 20 (20C-20D in some embodiments). The compressible fluid management layer 22 is designed to provide a cushion-like layer and a structure that also creates a fluid-capture, well-like feature. The compressible fluid management layer 22 defines by an inner edge 22A, an annular opening 28 (or relatively large aperture) desirably for direct fluid passage of body exudates that have passed through the topsheet layer(s) 16 (and an optional surge layer 20A), to the one or more surge 20B or absorbent layer(s) 20 (such as 20C-20D in some embodiments) subjacent to it. Desirably in one embodiment (such as that shown in FIG. 1), fluid that has passed through the topsheet layer 16, is channeled directly through the annular opening 28 to the one or more absorbent core layers 20C-20D (or the absorbent layer system including surge layer(s) 20B) without encountering an intermediate layer between the topsheet layer and the absorbent layers 20 (or absorbent layer system). Therefore the path of body exudate is desirably in one embodiment, directly in the Z direction, from the topsheet layer 16 to the surge 20B and absorbent layers 20C-20D to allow for rapid fluid absorption where it is needed most. Such compressible fluid management layer 22 also allows for temporary storage of body exudate in the fluid-capture, well-like structure created by the annular opening 28, while the fluid is being absorbed by the subjacent surge 20B and absorbent core layers 20C-20D. In one embodiment, the compressible fluid management layer 22 may itself absorb body exudate, but to a lesser extent than the absorbent layers 20 subjacent to it. It may also assist in preventing the attribute of "rewet". For the purposes of this disclosure, the term "rewet" shall mean the propensity of personal care absorbent articles to absorb fluid or liquid such as menses or urine through the topsheet layer and deliver it to an interior absorbent layer, and subsequently, to release it under the continuing pressure of wear, back to the topsheet layer from the absorbent layer(s). This release of fluid/liquid back to the topsheet often leads to the consumer perception of continuing wetness.

The absorbent article 10, may include one or more fluid surge 20A, 20B, distribution, or transfer layers either between the topsheet layer 16 and the compressible fluid management layer 22, or between the compressible fluid management layer 22 and the one or more absorbent core layer(s) 20C-20D. Layers subjacent to the topsheet 16 or the compressible fluid management layer 22 may include a color or print design to assist in highlighting the presence of the annular opening 28 and the compressible fluid management layer 22. Such additional visual emphasis will enable ease of placement of the annular opening 28 and compressible fluid management layer 22 under the areas of the wearer's body most likely to be the source of body exudate.

The compressible fluid management layer 22 includes a length L2 along the pad longitudinal direction and a width W2 along the pad transverse direction. Desirably, in one embodiment, the length L2 and the width W2 are both shorter than the subjacent absorbent layer(s) 20. In an alternative embodiment, only the width W2 is shorter than that of the subjacent absorbent layer(s) 20. For example, in one embodiment, the ratio of lengths of absorbent layer 20 to compressible fluid management layer 22 is between about 5:0.8 and 1:1, alternatively, between about 3:1 and 1:1. Desirably in one embodiment, the ratio of widths of absorbent layer 20 to compressible fluid management layer 22 is between about 5:0.8 and 1:1, alternatively, between about 3:1 and 1:1. Desirably, in one embodiment, the length L2 is between about 20 mm and 800 mm, alternatively between about 30 mm and 600 mm, alternatively, between about 50 mm and 360 mm. Desirably in one embodiment, the width W2 is between about 5 mm and 500 mm, alternatively between about 10 mm and 150 mm, alternatively between about 15 mm and 150 mm.

Figure 2:
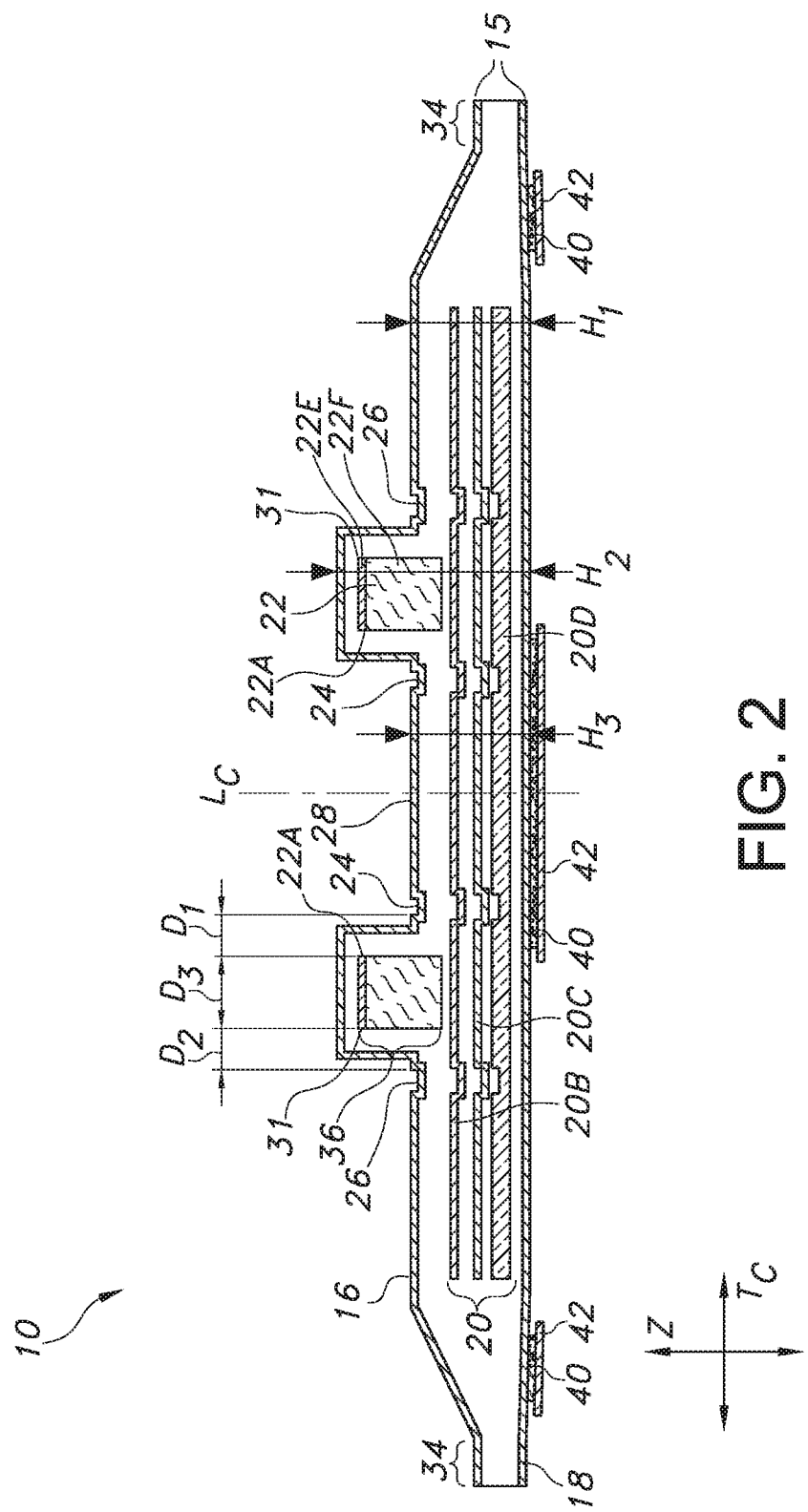
FIG. 2 illustrates a transverse direction, partially exploded cross-sectional view of the sanitary pad of FIG. 1 at line 2-2.

The compressible fluid management layer 22 includes transverse side edges 31 and longitudinal end edges 33. The transverse side edges 31 may be straight (FIG. 3A), or curved and include a concave portion as shown in FIG. 1. The end edges may similarly be straight (not shown), or curved as shown. The compressible fluid management layer 22 further includes a non-compressed thickness 36 in the Z direction (as seen in FIG. 2). Such non-compressed thickness is also referred to as the starting thickness for the purposes of testing herein. Desirably, in one embodiment, the non-compressed thickness (that is the layer thickness when not under compression of a wearer, such as when separated from the pad and measured by itself using thickness, caliper measurements described herein), is between about 1 mm and 20 mm, alternatively, between about 2 mm and 5 mm. An annular opening 28, defined by inner edge 22A of the compressible fluid management layer 22, includes an annular opening width 29 along the pad transverse direction T and an annular opening length 30 along the pad longitudinal direction L. Desirably, in one embodiment, the annular opening width 29 is between about 5 mm and 100 mm, alternatively, between about 10 mm and 30 mm. Desirably, the annular opening length 30 is between about 5 mm and 200 mm, alternatively, between about 30 mm and 70 mm. The longitudinal end edges 33 of the compressible fluid management layer 22 are separated from the end edges 27 of the absorbent layer 20 along the longitudinal direction, by a distance 32. Desirably, the distance 32 is between about 5 mm and 300 mm, alternatively, between about 5 mm and 100 mm. In one embodiment, the separation distance 32 differs at each end of the pad, such that the distance is greater at one end of the pad than the other. For example, as seen in FIGS. 5-8, the separation distance 32 on the front end 70 of an overnight pad 100, is larger than that at the back end 72 of the overnight pad 100. This is the result of the compressible fluid management layer 22 extending along the longitudinal direction L of the pad 10 to the back end, and into a region that would be situated within the intergluteal cleft (and between the buttocks) of a wearer when in use. Such extended layer is referred to herein as an extended length compressible fluid management layer.

Desirably in one embodiment, the entirety of the annular opening 28 is between and adjacent the two lateral extensions or wings 15 on the pad, and is entirely contained in the central crotch region of the sanitary pad 10. Desirably in one embodiment, the annular opening 28 is of an oval configuration, although other shapes are contemplated to be within the scope of the invention, such as, circular, square, or rectangular. It is desirable in one embodiment, for the annular opening 28 to be shaped and sized to closely surround that anatomical structure of a wearer from which body exudate normally exits the body. In such a manner, the compressible fluid management layer 22 will provide additional comfort to the wearer, by providing a cushion-like feature for contacting normally sensitive anatomical structures, surrounding the genital (perineal) areas. The annular opening may be made by traditional aperturing techniques, such as cutting, punching, or vacuum aperturing for example.

Figure 5:
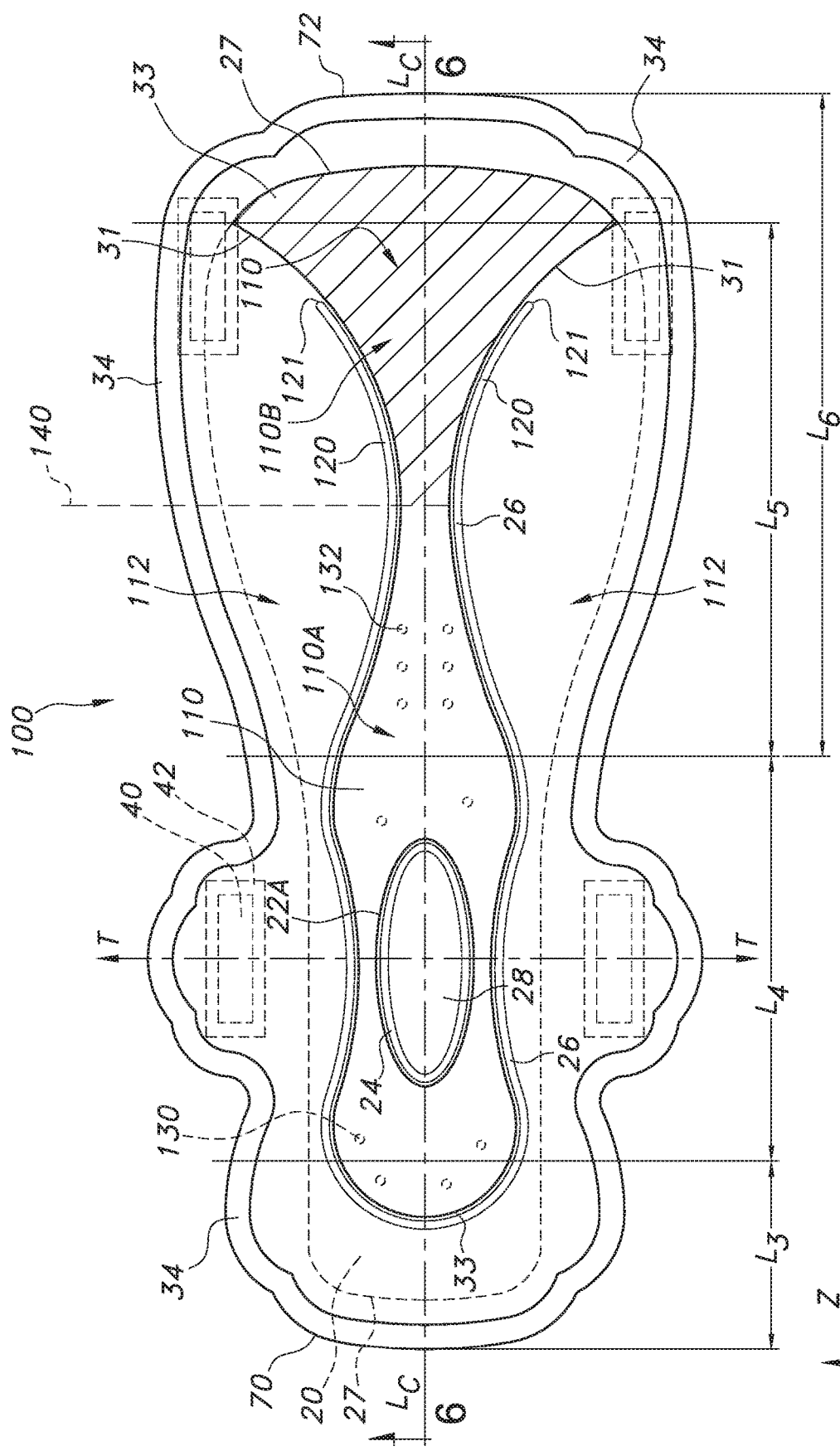
FIG. 5 illustrates a top plan view of an embodiment of an overnight sanitary pad in accordance with the invention.

The compressible fluid management layer 22 is desirably in one embodiment, pigmented, printed, or otherwise colored so that it can be easily distinguished from other layers in the sanitary pad 10. In one embodiment, the compressible fluid management layer is pigmented, printed, or otherwise colored a color such as pink, blue, red, green or black, and a layer subjacent to the compressible fluid management layer 22 is pigmented, printed, or otherwise colored with a different color or pattern such that the annular opening 28 is visually distinguishable from the compressible fluid management layer 22 within the sanitary pad 10. While in one embodiment, the compressible fluid management layer 22 is non-absorbent, in an alternative embodiment, such layer provides some level of absorbency, but of a relative amount less than that of absorbent layer(s) 20 subjacent to it. In one embodiment, such compressible fluid management layer 22 is of homogeneous or unitary construction. In a further embodiment, such compressible fluid management layer 22 is of a laminate construction of two or more layers, and desirably at least one of which includes a relatively high loft material. In a further embodiment, such layer 110 is optionally comprised of multiple different materials positioned along the article longitudinal direction as seen in FIG. 5 (110A, 110B). Alternatively, such layer 110 may be comprised of different materials positioned along the depth direction, such that they include different lateral widths. In such an embodiment, a lower material may be visible adjacent to an upper material when viewed from the wearer-facing surface, and appear as part of that upper material layer (not shown).

In the illustrated embodiments, numerous optional absorbent layers and other optional surge-type layers are illustrated in the figures. As shown for example in FIG. 4, a surge layer 20A is also present between the topsheet layer 16 and the compressible fluid management layer 22. Further, while the surge layer 20A is illustrated above compressible fluid management layer 22, it can also be present below compressible fluid management layer 22 in the Z direction, such as between the one or more remaining absorbent core layers 20 and the compressible fluid management layer 22. It should be appreciated that as few as one absorbent core layers 20D may be present in the article (i.e. sanitary pad), and the article may include no surge layer in one embodiment. As seen in FIG. 1, the absorbent layer(s) 20C-D (and any surge layers 20B) may be positioned entirely subjacent to a compressible fluid management layer 22.

The absorbent article includes a first embossed feature 24. Such first embossed feature 24 is desirably positioned adjacent the annular opening 28 inner edge 22A, desirably at a location inward from the inner edge 22A, such that the inner edge 22A surrounds the first embossed feature. Desirably as shown in FIG. 1, the first embossed feature 24 is aligned within the annular opening and itself encircles a portion 73 of the topsheet layer 16. The first embossed feature is desirably of the same overall shape as that of the annular opening inner edge 22A, and is desirably concentric with it. The first embossed feature may be a continuous or discontinuous channel or series of shapes, and desirably in one embodiment, extends within the annular opening adjacent/alongside the entire inner edge 22A by an equal distance. In an alternative embodiment, the first embossed feature 24 extends within the annular opening, but only partially around/alongside the annular opening inner edge 22A (not shown). The first embossed feature 24 creates a portion 73 of the topsheet layer 16 that is either completely or partially surrounded by the first embossed feature 24, and which extends across at least some of the annular opening 28 without having any embossed feature thereon. The first embossed feature 24 is illustrated as a series of flower depressions in FIG. 1. The first embossed feature 24 is desirably configured to resemble in overall shape, that shape of the annular opening inner edge 22A. The first embossed feature 24 is an embossment that passes into at least a topsheet layer 16, and a layer immediately subjacent to the compressible fluid management layer 22. In one embodiment, the first embossed feature 24 passes into the topsheet layer 16 and the absorbent layer(s) 20 and any surge, transfer, or distribution layer as previously described within the sanitary pad. As seen in FIG. 2, the first embossed feature 24 extends into the sanitary pad 10 in the Z direction. It may optionally extend to the backsheet layer 18, although such feature is not illustrated in FIG. 2. Desirably, in one embodiment, the first embossed feature 24 is positioned completely off of the annular opening inner edge 22A, and does not directly compress the compressible fluid management layer 22 at any point. That is, in one embodiment, the first embossed feature 24 is not situated over any portion (in the Z direction) of the compressible fluid management layer 22. In an alternative embodiment such first embossed feature 24 partially overlaps the inner edge 22A, but is of a shape similar in configuration to that of the inner edge. In one embodiment as seen in FIG. 1, the annular opening 28, the annular opening inner edge 22A, and the first embossed feature 24 are all oval in configuration.

Figure 7:
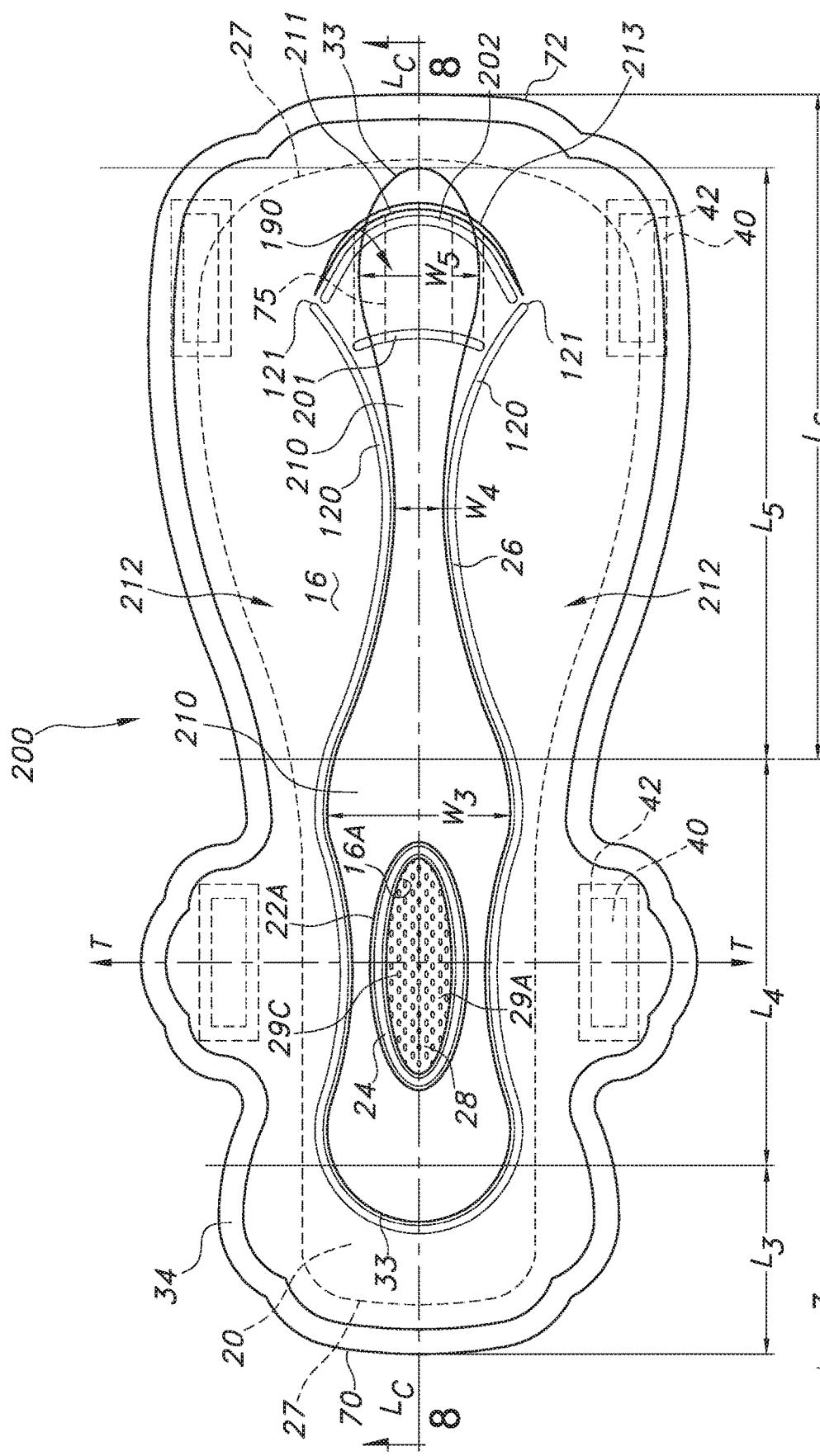
FIG. 7 illustrates a top plan view of an embodiment of an overnight sanitary pad in accordance with the invention.

The absorbent article 10 includes a second embossed feature 26. Such second embossed feature 26 is positioned laterally adjacent to (outward from) at least the transverse side edges 31 of the compressible fluid management layer 22, and in some embodiments, laterally adjacent one or both of the longitudinal end edges 33 as well. The second embossed feature 26 may completely surround the compressible fluid management layer 22 as shown in FIG. 1, or alternatively, may only partially surround the compressible fluid management layer 22, as shown in FIGS. 5 and 7. In FIG. 1, the second embossed feature 26 also lies adjacent/alongside the longitudinal ends 33 of the compressible fluid management layer 22, and generally has a similar overall shape as the peripheral shape of the compressible fluid management layer 22, or at least one end 33. The second embossed feature 26 can be a continuous channel that surrounds or partially surrounds the compressible fluid management layer 22, as shown in FIGS. 5 and 7, or alternatively, the second embossed feature 26 can be a discontinuous series of discrete shapes, such as dots, dashes, abstract or natural shapes, that surround or partially surround the compressible fluid management layer 22, as shown (as flowers) in FIG. 1. In one embodiment, the distance of the second embossed feature from the peripheral side edge of the compressible fluid management layer 22 is the same around the layer.

The first and second embossed features 24, 26 may include micro-embossing patterns within macro-embossed channel shapes, such as for example, alternating higher elevation and lower elevation topographies along the floor of the embossed feature, as described in U.S. Pat. No. 5,795,345 to Mizutani et al., which is incorporated by reference hereto in its entirety. The first and second embossed features 24, 26 assist in directing fluid within the absorbent article; in providing lateral barriers to fluid flow; in acting as stabilizing features to support the compressible fluid management layer, (and creating resistance to deformation, thereby reducing leakage); and also in further defining the fluid-capture, well-like feature (and annular opening 28) of the article by creating a pronounced, cushion-like contoured, wearer-facing surface on the absorbent article.

As noted, the first embossed feature 24 is desirably (entirely) situated within the confines of the annular opening (and spaced apart from the inner edge which defines the annular opening). The first embossed feature is in one embodiment, particularly within the topsheet layer 16, surge layer(s) and absorbent layer(s) 20, but not in the compressible fluid management layer 22 itself. The first embossed feature 24 is desirably in an overall shape that resembles that of the annular opening 28. The second embossed feature 26 is situated beyond the lateral-most edge(s) of the compressible fluid management layer 22 and desirably inwardly from the peripheral seal 34 of the absorbent article (i.e. sanitary pad 10). The second embossed feature 26 is also desirably in the topsheet layer 16, surge and absorbent layer(s) 20, but not in the compressible fluid management layer 22 itself. In overnight pad products, such as those illustrated in FIGS. 5 and 7, the second embossed feature 26 is desirably open ended, in that it does not completely surround the compressible fluid management layer 22 along at least one end. Rather, it desirably includes a surrounding portion at one end (the pad front end 70) and an outwardly flared portion which flares laterally away from the transverse side edges 31 of the compressible fluid management layer 110 towards the peripheral seal 34, at the pad back end 72. This lateral flaring assists in creating a more conformable back end 72 of the sanitary pad, which allows for conformance/bending of the pad in the wearer's intergluteal cleft and between the buttocks.

Figure 3A:
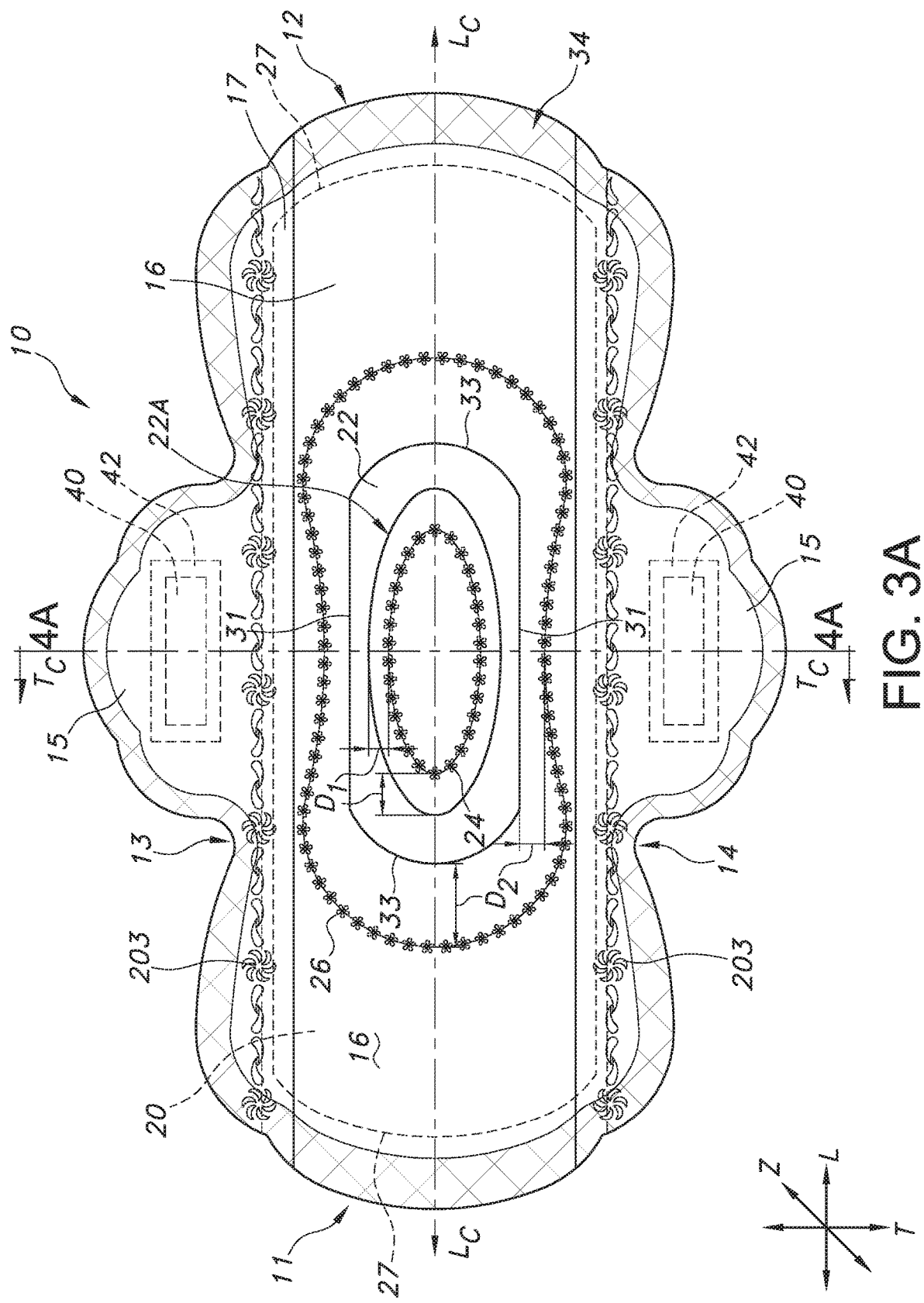
FIG. 3A illustrates a top plan view of an embodiment of a sanitary pad in accordance with the invention.

It should be noted that the absorbent article 10 may include additional embossed features besides the first and second embossed features 24, 26, such as those shown as 201, 202 in FIGS. 7-9, and 203 in FIG. 3A. Such additional embossed features may assist in maintaining the structural integrity of layers as in the embossed arc 202 in the back flap 190, or the side cover embossments 203, used to maintain a level edge on a side cover 17 portion of aside-by-side, dual-cover topsheet of FIG. 3A.

A transverse direction, cross-sectional view of FIG. 1 taken along line 2-2 is shown in FIG. 2. This view, which is partially exploded for ease of understanding, illustrates the penetration of the first and second embossed features 24, 26 in the Z direction of the sanitary pad 10. The embossed features in actuality, join the embossed layers together in the areas of embossment (as in a mechanical or thermal bond) such that they are not readily separable at those locations. As can be seen in the figure, the inner edge 22A of the compressible fluid management layer 22 is separated by a lateral distance D1 from the first embossed feature 24. Desirably, the lateral distance D1 is between about greater than 0 and 10 mm, alternatively, between about 1 mm and 10 mm, alternatively between about 1 mm and 3 mm. The separation distance of the first embossed feature 24 from the inner edge 22A is desirably in one embodiment, equal around the entire annular opening 28. However, in an alternative embodiment, the separation distance D1 may be larger in the article longitudinal direction (between the inner edge 22A and the first embossed feature 24 adjacent the compressible fluid management layer longitudinal ends 33 than adjacent the transverse side edges 31). The first embossed feature 24 is illustrated as present in numerous layers within the sanitary pad 10, but at least the topsheet layer 16 and one or several subjacent layers, such as the surge and absorbent layers (20B-20D), subjacent to the compressible fluid management layer 22. The compressible fluid management layer 22 is separated from the second embossed feature 26 by a lateral distance D2. Desirably, the lateral distance D2 is between about greater than 0 mm and 200 mm, alternatively, between about 1 mm and 200 mm, alternatively, between about 1 mm and 20 mm. The lateral distances D1 and D2 may not be the same for an absorbent article 10, but desirably are the same in one embodiment. The lateral distances D1 and D2 are illustrated as being significantly different from one another for example, in FIGS. 3A, 11, and 12. In such an embodiment, the ratio of lateral distances D1 to D2 may be between about 0.2:4.0 to 0.5:2.0. In some contemplated embodiments, by varying the lateral distances of the first and second embossed features, a variety of topsheet layer configurations may be utilized. The distance D3 between a transverse side edge 31 to the closest point on the inner edge 22A is desirably between about 2 mm and 15 mm.

The absorbent article 10 (i.e. sanitary pad) having the compressible fluid management layer, includes at least three thicknesses or heights along its surface. A first height H1 is the height of the sanitary pad 10 measured in the Z direction, and lateral to the compressible fluid management layer 22, through the pad including all surge, absorbent layer(s) 20, the topsheet layer 16 and the backsheet layer 18. The second height H2 is the height of the sanitary pad 10 in the Z direction through the compressible fluid management layer 22, including surge, absorbent layer(s) 20, the topsheet layer 16, and the backsheet layer 18. The third height H3 is the height of the sanitary pad 10 in the Z direction through the annular opening 28, including the topsheet layer 16, the surge, absorbent layer(s) 20 and the backsheet layer 18. The measurements may also include additional layers at the identified locations (such as transfer, and distribution layers). Desirably, in one embodiment, the height H1 (or thickness) of the absorbent article lateral to the compressible fluid management layer 22 is between about 0.5 mm and 15 mm, alternatively, between about 1 mm and 5 mm. Desirably, in one embodiment, the height H2 of the absorbent article through the compressible fluid management layer 22 is between about 1 mm and 30 mm, desirably between about 2 mm and 10 mm. Desirably, in one embodiment, the height H3 of the absorbent article through the annular opening 28 is between about 0.5 mm and 15 mm, desirably between about 1 mm and 5 mm.

The compressible fluid management layer 22 desirably includes a dimension that is either narrower in width, or both narrower in width and shorter in length than the dimensions of the one or more absorbent layers 20C-20D. As will be described below, the compressible fluid management layer 22, is often significantly thicker in dimension than many of the other layers within the absorbent article (sanitary pad 10). As seen in FIG. 2, in one embodiment, the compressible fluid management layer 22 may in fact be comprised of at least two separately manufactured layers 22E and 22F, an upper wearer-facing layer (22E) and a lower garment-facing layer (22F). The upper layer 22E may be of the same or similar materials to the lower layer, or it may be quite different. For example, it may be of a different chemistry or structural composition (such as fiber size). Alternatively, it may be of a different color than that of the lower layer. For instance, the upper layer may provide the color to the overall structure, whereas the lower layer may be white in color. The two layers may provide different functionality to the compressible fluid management layer, such as temporary storage, coloring, surge, or distribution. As noted, such layers may also be non-absorbent, and serve more to contain large volumes of fluid in the annular opening while absorption is occurring in the subjacent absorbent layers and to direct the fluid downward through the annular opening. Alternatively, such compressible fluid management layer 22 may include more than two layers, such as three or four layers having different functionality. The overall length and width of the multiple layers 22E, 22F in one embodiment may not be equal (not shown), although it is desired that the annular opening in each respective sublayer 22E, 22F be aligned in the Z direction.

The combination of the compressible fluid management layer 22 and placement of the two embossed features 24, 26, work to create a supported well-like structure which provides a defined cavity for holding body exudate, a more visually defined guide for placement of the absorbent article in a wearer's undergarments, and a comfortable structure for placement adjacent a wearer's body, and in particular about a wearer's perineal or vaginal area over prolonged timespans. An extended length compressible fluid management layer 22 (110, 210) provides for enhanced fit and fluid capture in overnight pad products.

A top plan view of another embodiment of a sanitary pad 10 in accordance with the invention is illustrated in FIG. 3. As can be seen in the figure, many of the same structures as were present in FIG. 1 are also included in this embodiment. However, this embodiment also includes a dual-cover configuration having side-by-side dual covers 16 and 17, in which a central longitudinally directed cover 16 is flanked on both lateral sides of the sanitary pad by side covers 17. The central and side covers 16, 17 may be of the same or different materials. The embodiment further a surrounded topsheet layer 29A which is desirably of a different material than the central or side covers 16, 17, such as a perforated film layer. The surrounded topsheet layer 29A may be formed from any traditional cover material, such as for example, a nonwoven material or apertured film material. An optional colored surge layer or transfer layer 29B is positioned under the surrounded topsheet layer 29A to provide additional color emphasis to the annular opening 28 when the sanitary pad is viewed from the wearer-facing surface. Perforation holes 29C in the film can be seen in the surrounded topsheet layer 29A, providing a different visual texture to the wearer-facing surface of the sanitary pad 10. Such perforated film topsheet will also help in reducing feelings of wetness. In this fashion, the illustrated sanitary pad of FIG. 3 actually includes three separate wearer-facing, skin-contacting topsheet layers 16, 17, 29A. In this illustrated embodiment, the central longitudinally directed topsheet layer 16 defines a topsheet layer inner edge 16A. The first embossed feature 24 is positioned between the compressible fluid management layer inner edge 22A and the topsheet layer inner edge 16A. Therefore, the first embossed feature 24 is situated in the central topsheet layer 16, as well as the surrounded topsheet layer 29A, the subjacent colored layer, and subjacent absorbent layers 20. The surrounded topsheet layer 29A extends partially under the encircling longitudinally directed topsheet layer 16 when viewed in the pad Z direction. The first embossed feature 24 is positioned approximately the same lateral distance D1 from the inner edge 22A as the distance that the second embossed feature 26 is positioned from the transverse side edge 31.

Figure 4:
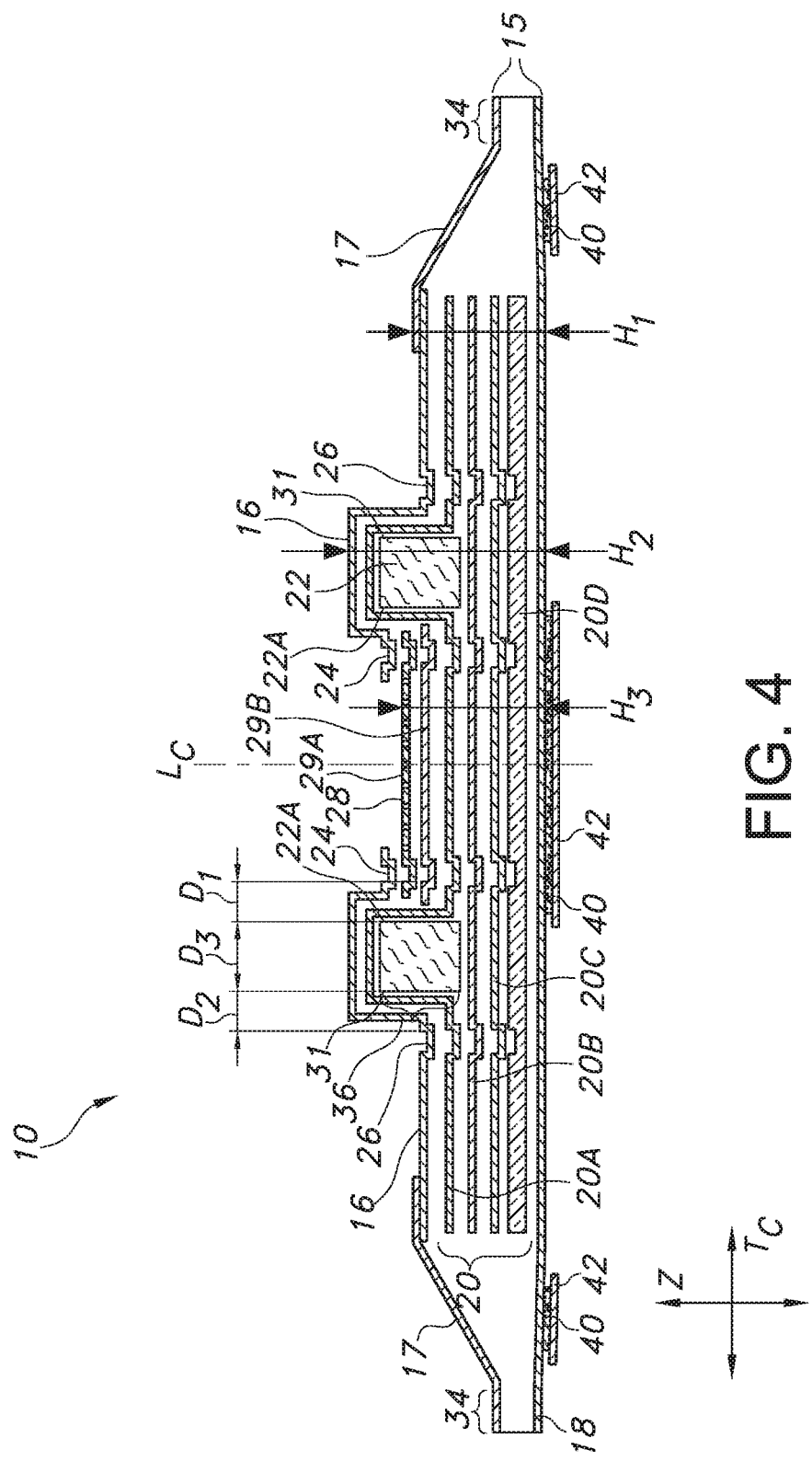
FIG. 4 illustrates a transverse direction, partially exploded cross-sectional view of the sanitary pad of FIG. 3 at line 4-4.

A transverse direction, partially exploded cross-sectional view of FIG. 3, along line 4-4 is illustrated in FIG. 4. As can be seen in the figure, the first embossed feature 24 extends into at least seven layers in the sanitary pad Z direction, including the layers within the annular opening 28, but not including the compressible fluid management layer 22. The second embossed feature extends into at least five layers in the sanitary pad Z direction, but not including the compressible fluid management layer 22.

A top plan view of another embodiment of the invention is shown in the sanitary pad illustrated in FIG. 3A. As seen in the figure, a side-by-side, dual-cover topsheet layer including a central longitudinally directed topsheet 16 and side covers 17 is included on the topsheet layer. The side covers 17 include an additional embossed feature 203 for sealing the side covers 17 flush against the central longitudinally directed topsheet layer 16 lateral side edges. As can be seen from the figure, while the first embossed feature 24 is positioned relatively close to the inner edge 22A of the compressible fluid management layer 22, the second embossed feature 26 is positioned a relatively larger distance from the end edges 33 of the compressible fluid management layer 22 (along the pad longitudinal direction L). The distances between the first and second embossed features and the respective transverse side edges of the annular opening and the compressible fluid management layer 31 are relatively similar however.

Figure 4A:
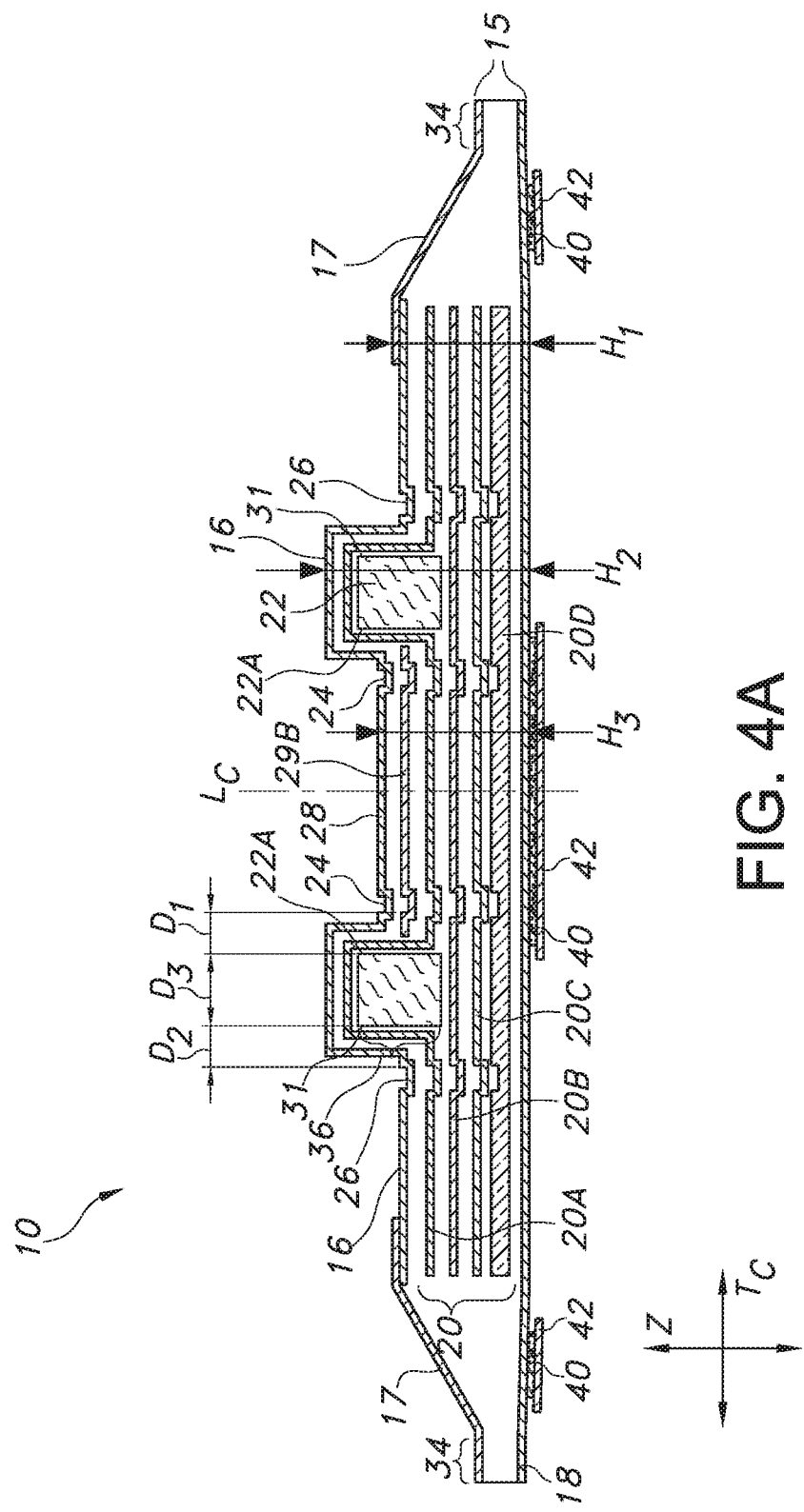
FIG. 4A illustrates a transverse direction, partially exploded cross-sectional view of an alternative embodiment of a sanitary pad.

A transverse direction, partially exploded cross-sectional view of FIG. 3A along lines 4A-4A can be seen in FIG. 4A.

As seen in the figure, the topsheet layer consists only of a side-by-side dual-cover topsheet layer with a central longitudinal topsheet layer 16 and two side covers 17. A colored layer 29B is also included to highlight the annular opening 28.

Figure 3B:
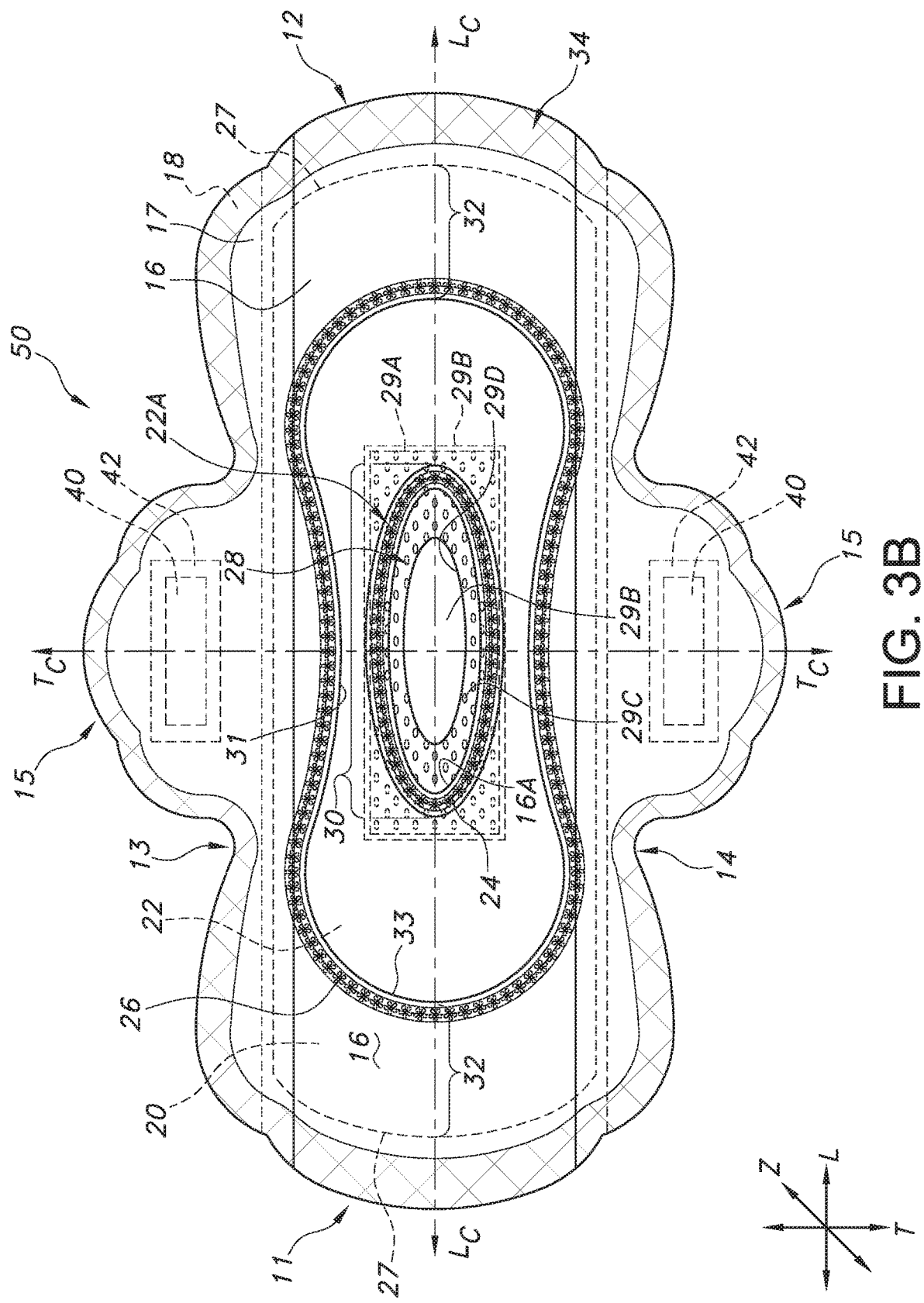
FIG. 3B illustrates a top plan view of an embodiment of a sanitary pad in accordance with the invention.

A top plan view of an alternative embodiment of a sanitary pad 50 is shown in FIG. 3B. As can be seen in FIG. 3B, such figure includes multiple topsheet layers including an encircling topsheet layer 16 which layer encircles a more centrally disposed surrounded topsheet layer 29A. The centrally disposed surrounded topsheet layer 29A itself has an opening therein, which exposes a subjacent layer 29B through an even smaller opening than that defined by the inner edge 16A of the outer topsheet layer 16. In this fashion, multiple textures and functions of various layers may be exposed to the skin of a wearer. For example, side covers 17 may be fashioned from a particular nonwoven sheet material. Central topsheet 16 may be fashioned from the same nonwoven or of a different nonwoven sheet material. Surrounded topsheet layer 29A may be fashioned of a perforated film or other nonwoven sheet material, and exposed via inner edge 29D, innermost layer 29B may be fashioned still of yet another material so as to provide an appropriate target zone for receiving large quantities of exudate from a wearer's anatomy.

A top plan view of an overnight sanitary pad 100 in accordance with the invention, is illustrated in FIG. 5. As can be seen in the figure, the overnight sanitary pad 100 includes a single material topsheet layer 16. As can also be seen in the figure, an extended length compressible fluid management layer 110 extends above and across substantially the full length of the underlying absorbent layer(s) 20. The extended length compressible fluid management layer 110 may be of unitary construction. Such layer may be homogeneous in material composition and material properties, along its length, or alternatively, it may be heterogeneous in that its forward directed portion 110A surrounding the annular opening 28 may be constructed of material with different properties than its rearward directed portion 110B. In such a manner, more rigid construction materials may be placed in a desired location, such as for example in the rearward directed portion 110B so as to maintain pressure and/or elevation in a wearer's intergluteal cleft throughout the night. Alternatively, the extended length compressible fluid management layer 110 may itself be comprised of two different materials 110A and 110B, separated by a seam for example, approximately at the dotted line 140 for ease of understanding only. The two different materials may be differentiated by characteristics such as absorbency, resiliency, or color, so as to accommodate different areas on a wearer's anatomy, alternatively to assist in pad placement, alternatively to highlight different areas of the pad 100. The visible seam may optionally be present to clearly distinguish the two different materials or functionalities.

The extended length compressible fluid management layer 110 may optionally be perforated (in addition to containing the relatively larger annular opening 28), such that a series of relatively smaller perforations are placed in the layer 110 for rapid fluid absorption to lower layers along the layer length. In any event, it is contemplated that the annular opening will in all instances, be larger in area than each one of the individual perforations. Such relatively smaller perforations may be sized to be between about 0 mm and 30 mm, alternatively, greater than 0 mm, to about 20 mm, alternatively, between about 1 mm and 5 mm each. Such perforations may be located in a fairly random configuration 130, such as those illustrated around the annular opening 28, or may be positioned in an ordered series or sequence 132, such as those illustrated along the extended length compressible fluid management layer forward directed portion 110A (or a combination of the two). While not shown in the figure, the perforations may also be present in the rearmost portion of the layer 110B. The perforations may be formed using traditional perforation techniques. The perforations may be present in multiple sizes and will enhance the capability of absorption along the full length of the layer as well as provide some breathability through such layer.

In the overnight pad embodiment 100, the absorbent layer(s) include a length along the article 100 longitudinal direction of between about 20 mm and 800 mm, alternatively between about 50 mm and 360 mm. Such extended length compressible fluid management layer 110 is desirably of a length along the longitudinal direction of the article 100 of between about 40 mm and 800 mm, alternatively, between about 130 mm and 430 mm. Elongated areas 112 of the subjacent absorbent layer(s) 20 are not covered by the compressible fluid management layer 110. The overnight sanitary pad 100 includes a relatively narrower front end 70 and a relatively wider back end 72. While the first embossed feature 24 is in the form of a continuous channel that completely encircles the inner edge 22A defining the annular opening 28, the second embossed feature 26 does not completely surround the extended compressible fluid management layer 110. Rather, only towards the front end 70 of the article 100 does the second embossed feature 26 surround the compressible fluid management layer 110. Towards the back end 72, the second embossed feature 26 flares outward 120 towards the peripheral seal 34, but does not surround the compressible fluid management layer 110. The second embossed feature 26 includes two separate outwardly flared ends 121 which terminate short of the peripheral seal 34 region, and are shorter than the transverse side edges 31 of the compressible fluid management layer 110. In an alternative embodiment (not shown), the elongated compressible fluid management layer 110 may extend to the back end edge 27 of the absorbent layer 20, such that its back end edge dimensions are the same as the absorbent layer 20 back end edge subjacent to it.

In a further alternative embodiment, the compressible fluid management layer may be colored differently from subjacent surge or absorbent layers so as to emphasize its structure and assist in article placement. Such subjacent layers may alternatively, be colored in a similar fashion to that of the compressible fluid management layer, so as to provide a unified look to the overall design. Such difference in coloration may also assist in highlighting the annular opening and extended back end of the layer for article placement, and any optional perforations in the compressible layer 22,110 in order to highlight additional layer functionality.

When viewing the overnight pad 100 of FIG. 5, it is helpful to understand that the pad includes a front-most region having a length L3, an annular-opening containing region having a length L4, a back-most region including all or most of the extended length compressible fluid management layer 110 (depending on embodiment) having a length L5, and a back region which includes the extended compressible fluid management layer and the back end of the pad, having a length L6. The lengths L5 and L6 correspond to the intergluteal cleft and coccyx region (between the buttocks) of a wearer, whereas the length L4 corresponds to a wearer's crotch region. The back-most region defined by L5 includes a narrowing section in the compressible fluid management layer 110, which is narrower along the transverse direction than portions of the front-most pad region (L3) and the annular-opening containing region (L4). The narrowing section is designed to be placed in the wearer's intergluteal cleft to provide for enhanced capture of fluid while a wearer is sleeping.

Figure 5A:
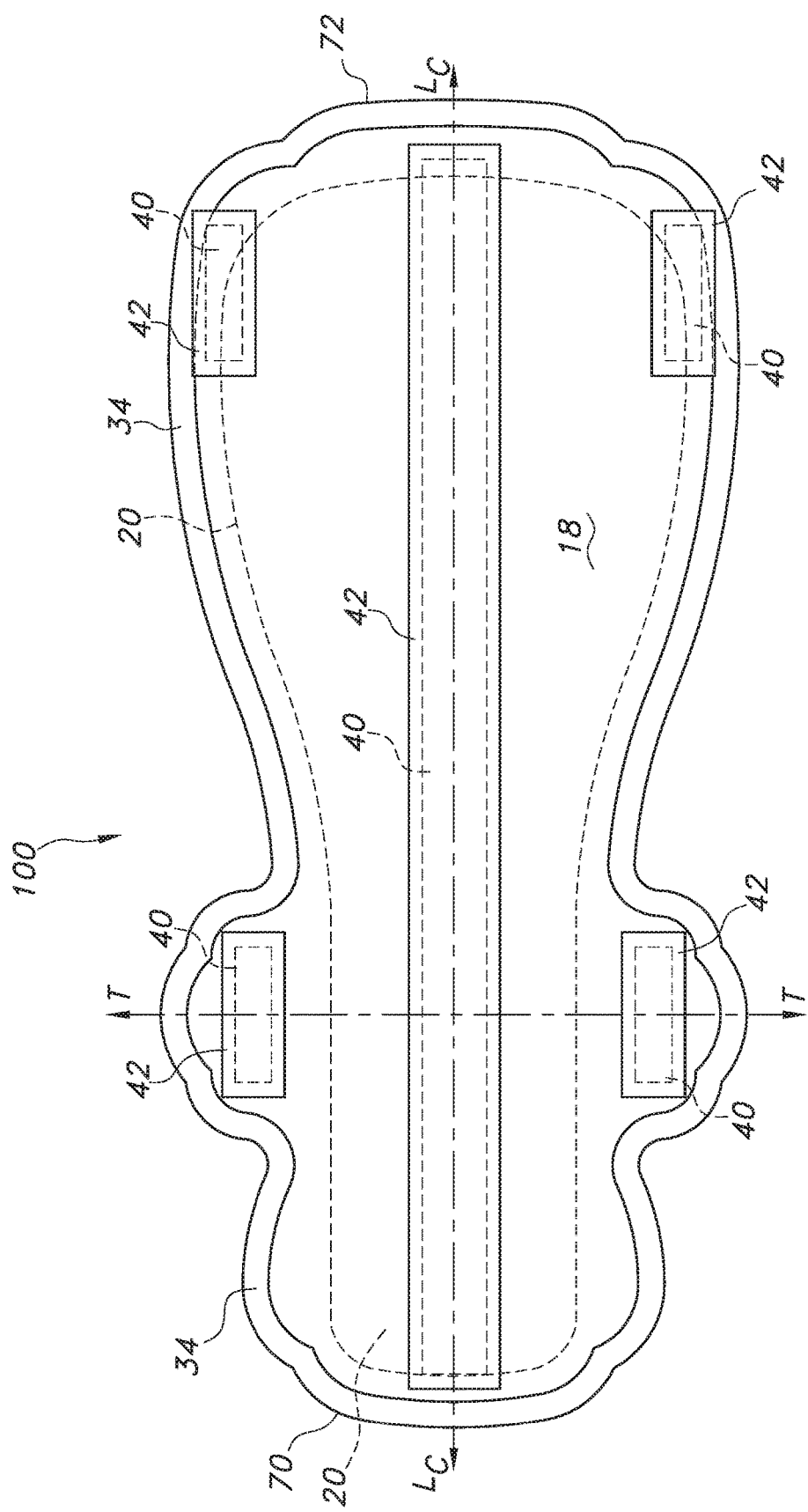
FIG. 5A illustrates a bottom plan view of the overnight sanitary pad of FIG. 5.

A back plan view of the overnight sanitary pad 100 of FIG. 5 is illustrated in FIG. 5A. As can be seen in the figure, multiple adhesive patches 40 are positioned along the garment-facing surface of the backsheet layer 18. In particular, four outer adhesive patches are situated with two adjacent the crotch region, and two adjacent the back end 72. An adhesive patch is also positioned along the central longitudinal direction of the article on the garment-facing surface of the backsheet 18. Each of the adhesive patches 40 are covered by an individual release sheet 42 to protect the adhesive patch 40 until it is needed.

Figure 6:
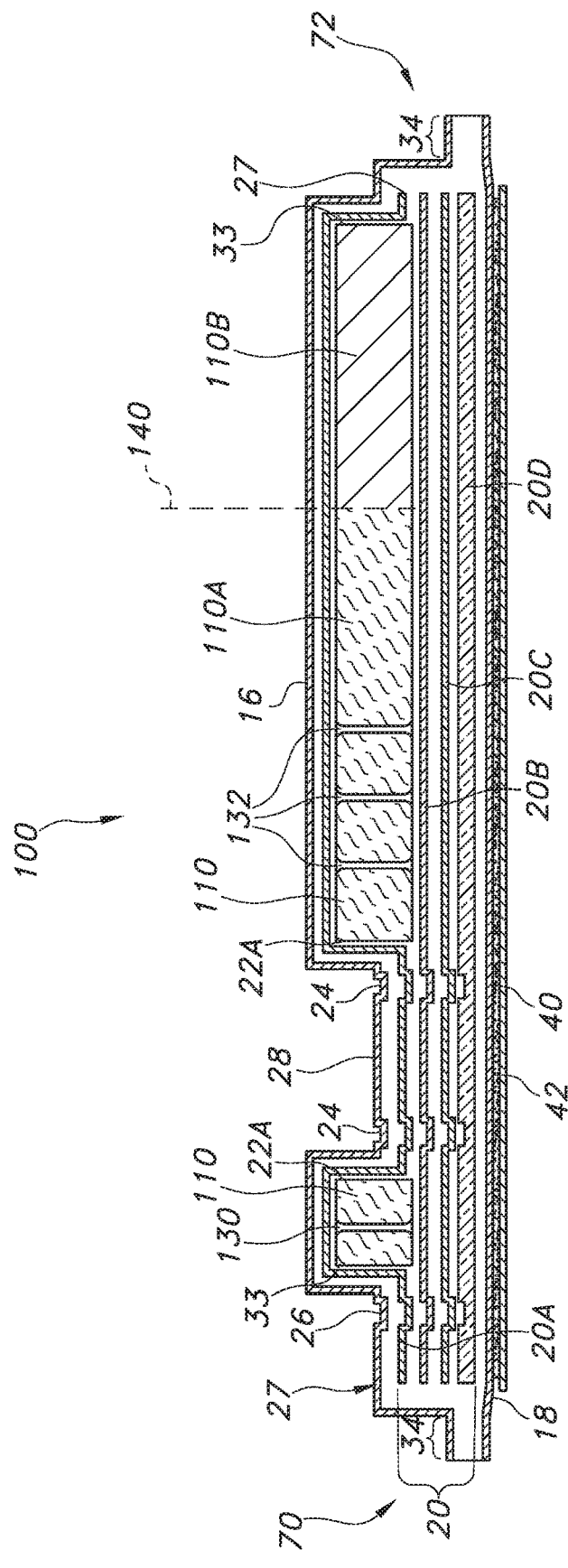
FIG. 6 illustrates a longitudinal direction, partially exploded cross-sectional view of the overnight sanitary pad of FIG. 5 at line 6-6.

A longitudinally directed, partially exploded cross-sectional view of FIG. 5 along line 6-6, is illustrated in FIG. 6. As can be seen in FIG. 6, the extended length compressible fluid management layer 110 extends substantially the full length of the surge and lower absorbent layer(s) 20. While the first embossed feature 24 is adjacent the entire inside edge 22A of the annular opening 28, and is adjacent the front end edge 33 of the compressible fluid management layer 110 (near article front end 70), it is not adjacent the back end edge of the compressible fluid management layer (near article back end 72). While in the exploded cross-sectional views the embossed features 24, 26 are illustrated as separated from one another in each layer along the Z direction, it should be appreciated that this representation is for ease of viewing only, and in the article, the embossed features actually join and hold the embossed layers together (along with any construction adhesive or other bonding mechanisms employed). The optional perforations in either a random configuration 130 or an ordered series or sequence 132 can be seen in the various regions of the extended length compressible fluid management layer 110.

A top plan view of a further alternative embodiment of an overnight sanitary pad 200 is illustrated in FIG. 7. As can be seen in FIG. 7, the overnight sanitary pad 200 includes an encircling, dual-cover topsheet in which a larger topsheet layer 16 encircles or surrounds a central surrounded topsheet layer 29A. The overnight sanitary pad 200 includes an extended length compressible fluid management layer 210 having various widths W3, W4, and W5 along its length. While the second embossed feature 26 includes a surrounding portion at the pad front-most end 70 (around the compressible layer end 33), it includes flared ends 120 having separated discrete ends 121 towards the back-most end 72.

The overnight sanitary pad 200 includes a moisture activatable back flap 190, which upon contact with moisture, lifts up from the plane of the pad to create an elevated flap that helps to capture moisture from a wearer during nighttime hours. Such back flap includes a cut portion of the upper topsheet layer 16, that is defined by flap outer edge 211, and upper topsheet 16 edge 213. The activatable flap includes a laminate of fluid shrinkable fibers 75 that are laminated between at least two nonwoven sheets 76 (as also seen in FIGS. 9 and 10A). The extended length compressible fluid management layer 210 is not itself flared in the coccyx/buttocks region as with previous embodiments, but instead, ends in a relatively narrow and rounded configuration subjacent to the back flap 190. The structural integrity of the activatable back flap 190 is strengthened by embossed features 201, 202, which also help to anchor the ends of fluid shrinkable fibers 75 in place. Such activatable back flap and fluid shrinkable fibers and the overall back flap/tail-like structure are further described in international patent publication WO2012/155316 to Aschebrenner et al., which is hereby incorporated by reference hereto in its entirety.

Figure 8:
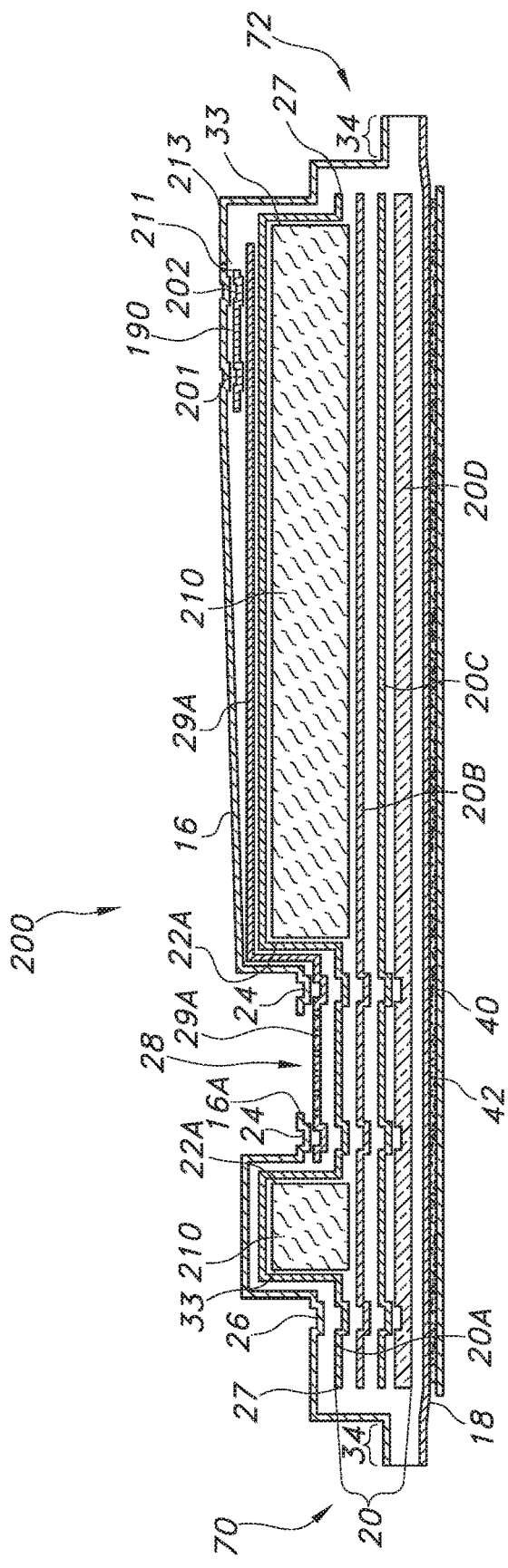
FIG. 8 illustrates a longitudinal direction, partially exploded cross-sectional view of the overnight sanitary pad of FIG. 7 at line 8-8.

FIG. 8 illustrates a longitudinal cross-sectional view of the overnight sanitary pad 200 of FIG. 7 taken along line 8-8. As can be seen in the figure, the activatable back flap 190 remains in the plane of the pad until it is activated by moisture contact. Optionally, the centrally located surrounded topsheet layer 29A can extend under the surrounding topsheet 16 such that it also is present as a multilayered topsheet under the activatable back flap 190. A side view of the activated back flap 190 is illustrated in FIG. 10.

Figure 11:
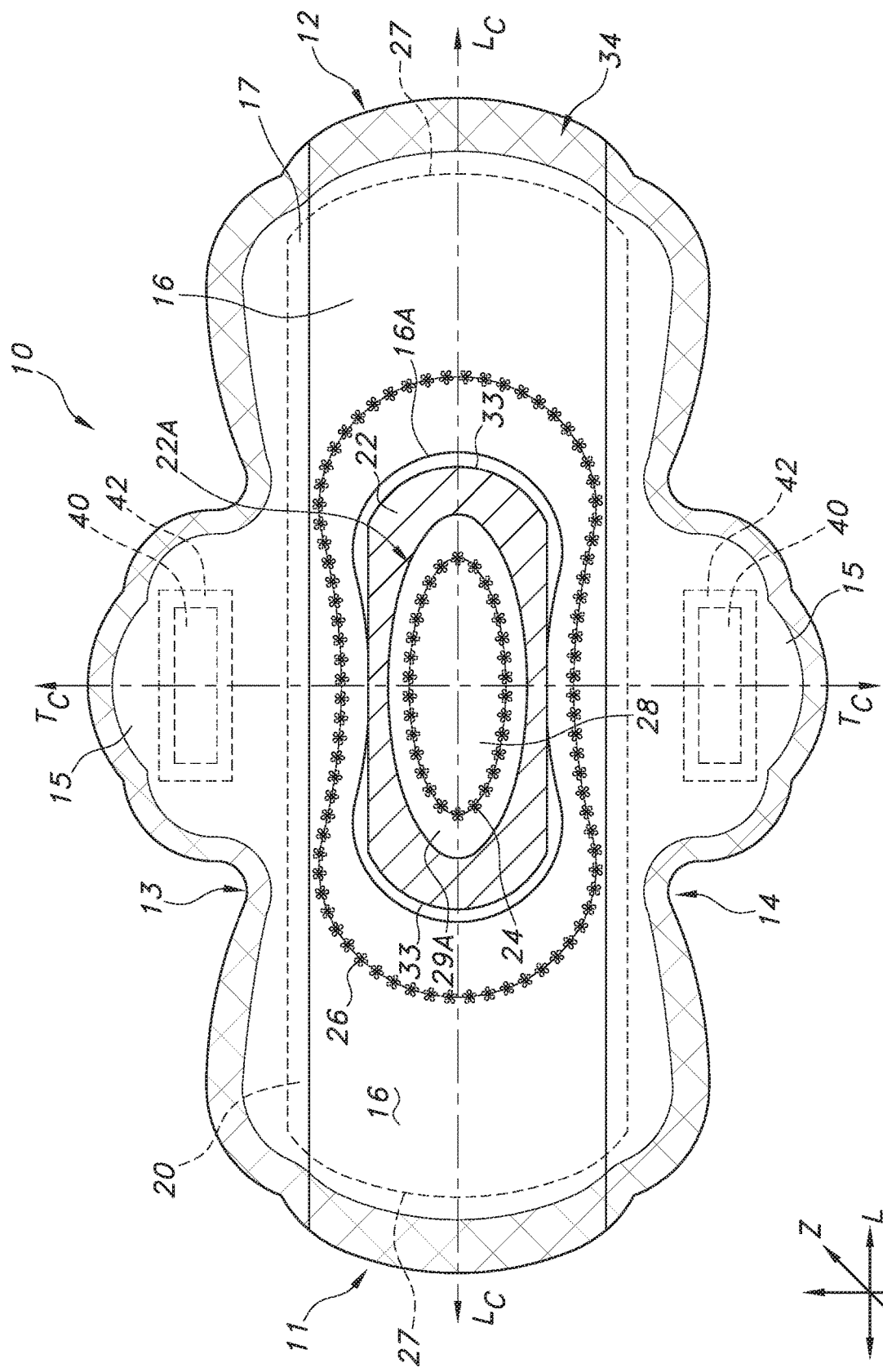
FIG. 11 illustrates a top plan view of an embodiment of a sanitary pad in accordance with the invention.

A top plan view of an alternative embodiment of a sanitary pad 10 is illustrated in FIG. 11. As can be seen in the figure, the pad includes a central surrounded topsheet layer 29A, which is exposed to the skin of a wearer along the center area of the pad. The center surrounded topsheet layer 29A area is defined by the inner edge 16A of the surrounding topsheet layer 16. In this embodiment, the first embossed feature 24 is situated inward of both the surrounding topsheet layer inner edge 16A and the compressible fluid management layer inner edge 22A.

Figure 12:
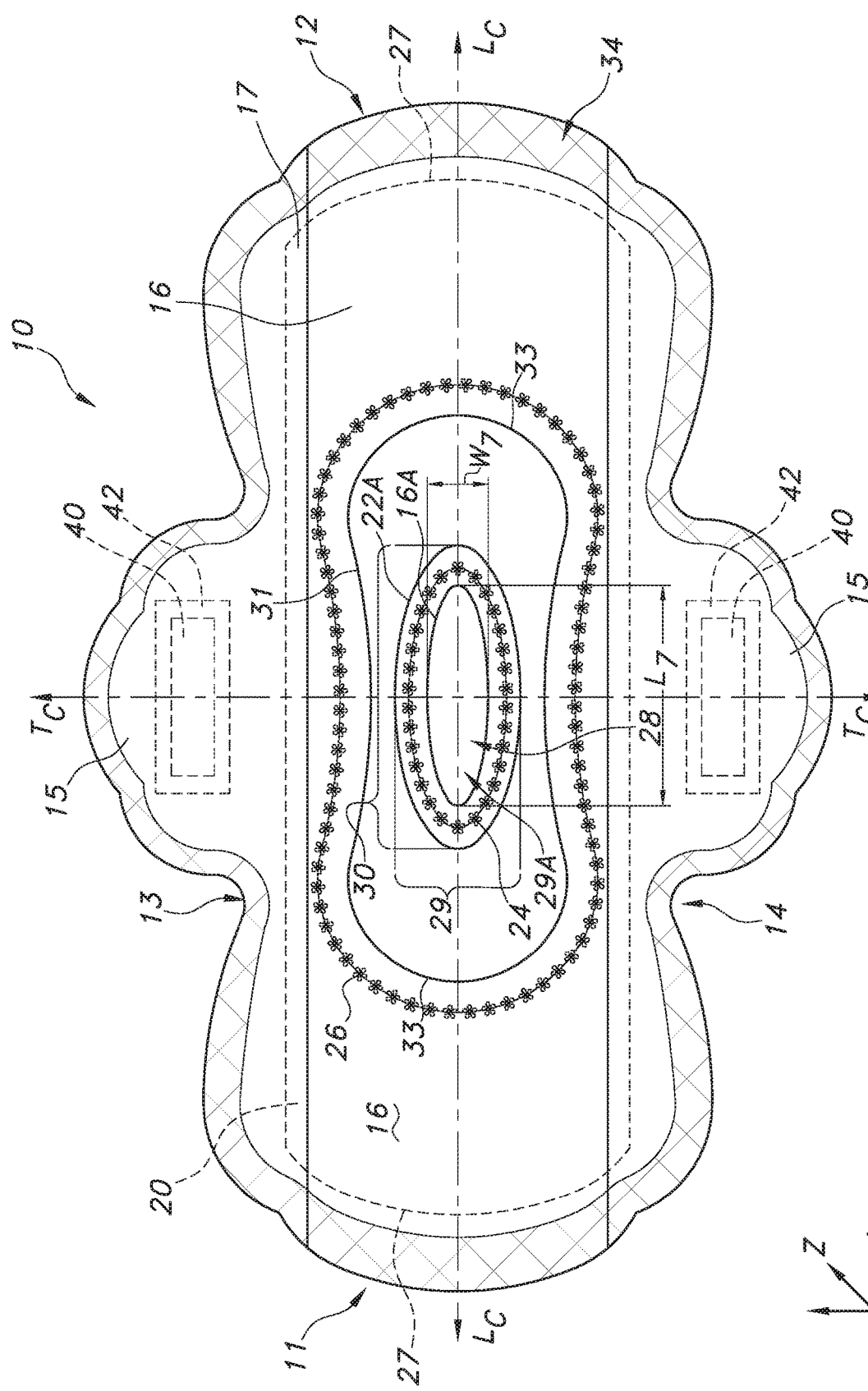
FIG. 12 illustrates a top plan view of an embodiment of a sanitary pad in accordance with the invention.

A top plan view of yet another alternative embodiment of a sanitary pad 10 is illustrated in FIG. 12. As can be seen in the figure, the pad includes a central surrounded topsheet layer 29A, which is exposed to the skin of a wearer along the center area of the pad. The center surrounded topsheet layer 29A is defined by the inner edge 16A of the surrounding topsheet layer 16. In this embodiment, the first embossed feature 24 is situated between the surrounding topsheet layer inner edge 16A and the compressible fluid management layer inner edge 22A.

Figure 13:
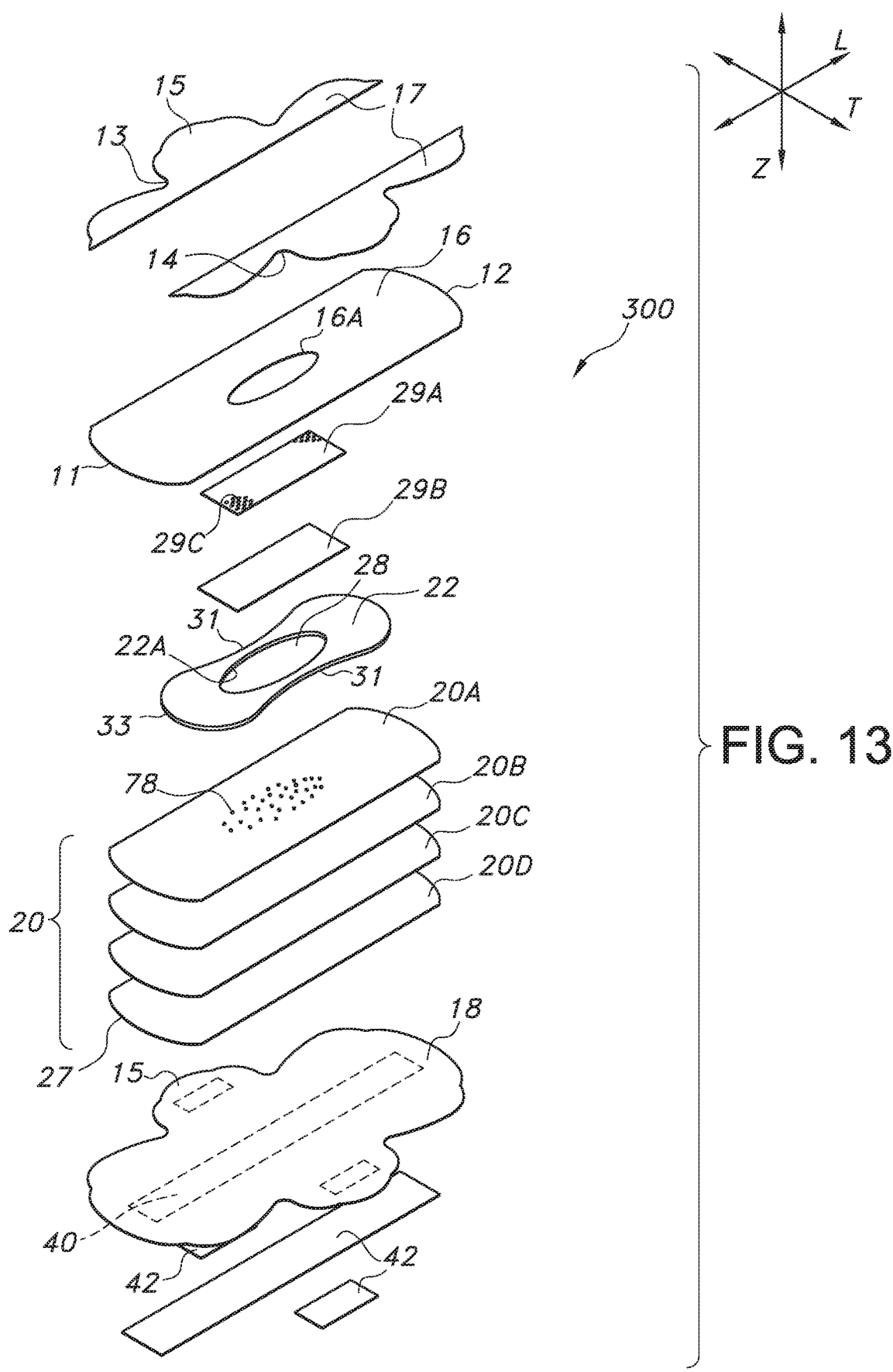
FIG. 13 illustrates an exploded perspective view of an embodiment of a sanitary pad in accordance with the invention.

An exploded perspective view of yet another embodiment of a sanitary pad 300 of the invention is illustrated in FIG. 13. While the construction adhesive elements are not illustrated in the figure, each of the various layers, including optional and desirable layers are shown. Such embodiment includes a multiple layer topsheet having side cover topsheet layers 17, a central longitudinally disposed topsheet layer 16, a surrounded topsheet layer 29A, which is surrounded on all lateral sides by the central longitudinally disposed topsheet layer 16. Since the central longitudinally disposed topsheet layer 16 defines an oval aperture by an inner edge 16A, the surrounded topsheet layer 29A is exposed to the skin of a wearer through the oval aperture defined by the inner edge 16A. An optional colored or printed layer (such as a surge layer) 29B is present subjacent the surrounded topsheet layer 29A. A compressible fluid management layer 22 is positioned subjacent to the optional colored or printed layer 29B and itself defines an annular opening 28 created by an inner edge 22A. The compressible fluid management layer 22 includes transverse side edges 31 and longitudinal end edges 33. Subjacent to the compressible fluid management layer 22 are a series of absorbent and/or surge layers 20A-20D. For example, an optional first surge layer 20A including a series of printed dots or patterns 78 present to provide for fluid control and also to highlight the annular opening 28 above it, via the printed pattern. An optional second surge layer 20B is subjacent to the first surge layer. An optional first absorbent layer 20C, such as an airlaid layer, is present subjacent to the optional second surge layer 20B. A primary absorbent layer 20D, either of an airlaid material, cellulose-based material, or SAP/airlaid composite is positioned beneath the optional first absorbent layer 20C in the article Z direction. Finally, a liquid impermeable backsheet 18, having garment adhesive strips or patches 40 on the underside surface, is situated subjacent to the primary absorbent layer 20D. Adhesive release strips 42 are located over the adhesive patches 40. Various layers within the sanitary pad 300 can be used to highlight the compressible fluid management layer 22 and annular opening feature 28. For example, layers 16, 29B, and 20A are desirably colored or printed to highlight the position of the compressible layer and annular opening for assisting the wearer in placement of the pad in the appropriate location in a wearer's undergarments. Such layer (layer 20A) may itself be entirely colored or printed so as to highlight the outline of the compressible fluid management layer above it in the Z direction or at least partially printed to enhance the shape of the upper compression layer.

The skin-contacting, liquid permeable topsheet layers 16, 17, 29A, 29D may be manufactured from any number of conventional materials commonly used as a user-facing surface on an absorbent article. For example, non-limiting examples of such topsheet materials include fibrous nonwoven sheet materials made from synthetic fibers such as polyolefinic materials, such as spunbond, spunlace, meltblown, and carded web materials (such as thermally bonded carded webs (TBCW), through-air bonded carded webs (TABCW)), fibrous woven sheet materials, micro-apertured polyolefinic film or apertured fibrous nonwoven materials (single and dual apertured), and laminate combinations of the foregoing materials. In the case of apertured topsheet layer materials, such apertures may be created via multiple methods such as pin, vacuum, hydroforming, and a combination thereof. Such aperturing may be of single sized or shaped apertures, or multiple sized or shaped apertures. Further, monolayered or multilayered sheet materials of the foregoing and laminates thereof, can also be used as the liquid permeable first topsheet layer. Particularly, carded web materials may be made from staple, bicomponent fibers as are known in the art. The topsheet layer(s) may also be separately embossed in addition to the first and second embossed features previously described. In one embodiment, the liquid permeable topsheet layer 16 desirably includes a dual-apertured film in which the film includes two differently shaped or sized apertures. Such films are available from numerous suppliers including Tredegar Corporation, United States, Pantex International, Italy, Texol, Italy, and Xiamen Yanjan Ind., China Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety. Desirably, topsheet layer materials are either inherently hydrophobic based on their composition, or made so with hydrophobic treatments, as such hydrophobicity assists in maintaining sensations of dryness and can assist in preventing rewet. In certain embodiments, such films may also be made partially or completely hydrophilic with the application of internal or topical surfactants. Further examples of hydrophobic topsheet layer materials and other absorbent article internal layers may be found in U.S. Pat. No. 8,383,877 to Singh Kainth et al., and United States patent publication US2013/0197462 to Abuto et al. each of which are incorporated herein in their entirety by reference thereto, for purposes not inconsistent herewith. Alternatively, as previously described in connection with FIG. 3A, the topsheet layer may also be made from two or more different nonwoven or film materials at least one of which is inherently hydrophilic or which has been treated to provide such property, with the different materials placed in separate locations laterally across the topsheet layer 16 and along the absorbent article transverse direction T. For example, the topsheet layer 16 may be a two layer (such as in the same or two different horizontal planes) or multi-component material with a central longitudinally directed topsheet section as described in the figures positioned along and straddling the central longitudinal direction of the article, with lateral side-topsheet sections 17 (side covers) flanking and joined to each side (or side longitudinal edge) of the central longitudinally directed topsheet layer. The central topsheet section may be made for example, from hydrophilic TABCW materials or it may be made from a perforated film that has been treated to be hydrophilic. The lateral side topsheet covers 17 may be made from a different fibrous nonwoven material which is joined to the central longitudinally directed section, such as by adhesive or thermal bonding.

The basis weight of nonwoven webs to be used as liquid permeable topsheet layers may generally vary, such as from about 5 grams per square meter ("gsm") to 150 gsm, in some embodiments from about 10 gsm to about 125 gsm, and in some embodiments, from about 15 gsm to about 120 gsm. Desirably, in one embodiment, the topsheet layer is a through-air bonded carded web having a basis weight of between about 20 gsm and 40 gsm.

As noted, optionally one or more surge layers 22A, 22B, or fluid transfer layers may be utilized in the absorbent article construction. Such layers may be used to address a sudden onset or gush of fluid into an absorbent article, or to provide some other functionality, such as a color to highlight a layer above the surge layer in the Z direction. Such additional surge and fluid transfer layers include, but are not limited to, apertured films, hydrophobic bonded-carded webs, hydroentangled nonwoven webs, or spunbond webs. Surge and fluid transfer layers are well known in the art and will not be further described herein.

The compressible fluid management layer 22, 110, 210 is situated beneath the topsheet layer, and above the absorbent layer(s) 20C-20D in the article Z direction. It may also be situated below a surge layer 20A or above a surge layer 20B depending on the particular embodiment. The compressible fluid management layer 22, 110, 210 may be manufactured from a variety of different materials, such as for example, high loft nonwoven materials, airlaid materials, foams, apertured films, and laminates of such. For example such layer may be produced from a nonwoven sheet material having a basis weight of between about 30 and 150 gsm, and a thickness of between about 1.0 and 3.0 mm, alternatively between about 1.5 mm and 2.5 mm (and of fiber sizes between about 1.5 and 6.0 denier), alternatively, from an airlaid sheet material having a basis weight of between about 50 and 200 gsm and a thickness of between about 0.50 and 3.0 mm, alternatively, between about 1.0 and 2.8 mm, alternatively from a superabsorbent (SAP)-containing sheet having a relatively lower amount of SAP to lessen stiffness, and an overall basis weight of between about 100 and 400 gsm and a thickness of between about 0.50 and 1.40 mm, alternatively from cellulose pulp sheets, having a basis weight of between about 150 and 450 gsm and a thickness of from 4.0 to 6.0 mm, alternatively from foam materials, such as for example cellulose foam, memory foam, PVA foam, and nanofoam (including both open cell and closed cell foams depending on fluid retention properties desired in the layer). Such compressible fluid management layer may also be constructed particularly from materials described in international publication no. WO 03/053314 to Ohshima et al., which is hereby incorporated by reference thereto in its entirety. Combinations of the above materials are also contemplated for use as the compressible fluid management layer.

Alternatively, such compressible fluid management layer may be made from an airlaid sheet that is produced as a structure from numerous continuous depositions of airlaid layers one upon the other, such as those available from Buckeye, Germany, and QiaoHong, China. Such airlaid layers may in one embodiment have a basis weight of between about 30 gsm and 300 gsm, alternatively, between about 100 and 200 gsm.

Still further, such material may be manufactured from a nonwoven laminate of at least one previously constructed nonwoven layer with one or more airlaid layers. For example, such a laminate may be produced from a TABCW, such as a colored TABCW that is separately produced, and then laminated to one or more airlaid layers. Such TABCW layer may be comprised of a variety of fibers such as for example colored PE/PP bicomponent fibers and white or non-colored PET fibers. In such a laminate, the upper layer may provide none, or limited fluid storage and color to the laminate, whereas the lower layer may provide some level of absorbency if desired, or little at all. In such a laminate, the upper layer may be present in a range of between about 20 gsm and 200 gsm such as about 55 gsm whereas a lower airlaid layer comprised of pulp, a bicomponent fiber, and minimal amounts of latex, may be present in a range for example, of between about 30 gsm and 300 gsm, such as about 85 gsm. Airlaid laminates (that is, a separately produced airlaid and nonwoven layer that are then laminated together) are available from companies such as Fitesa Airlaid Co., Ltd., China and Sambo Co. Ltd., South Korea. Such laminates may include two or more layers, with one or more layers being colored as desired. Such coloring may occur by either printing or color placed within individual fibers of a layer. Such laminates may have an overall thickness for example, of between about 1.5 and 10.0 mm, or alternatively between about 2.0 mm-5.0 mm, alternatively between about 2.0 mm and 3.0 mm.

The absorbent layer(s) 20 (20B-20D) can itself comprise a single layer or multiple layers and these one or more layers can themselves comprise similar or different materials. Highly absorbent core layers often include, but are not limited to, hydrophilic batts or webs containing wood pulp fibers, superabsorbent particles or fibers (also known as SAP or SAM), synthetic wood pulp fibers, synthetic fibers, coform materials, hydrophilic foam materials, and combinations thereof. The absorbent layer(s) 20 may comprise any one of a number of materials and structures, the particular selection of which will vary with the desired loading capacity, flexibility, body fluid to be absorbed and other factors known to those skilled in the art. By way of example, suitable materials and/or structures for the absorbent layer(s) 20 include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States patent publication 2010/0174260 to Di Luccio et al., each of which is hereby incorporated by reference thereto in its entirety.

The shape of the absorbent core layer (while generally shown as a dog-bone or oblong configuration to mimic the outer peripheral shape of the absorbent article), can vary as desired and can comprise any one of various shapes including, but not limited to, generally triangular, rectangular, and elliptical shapes. In one embodiment, the absorbent layer(s) 20 have a shape that generally corresponds with the overall peripheral shape of the absorbent article (i.e. sanitary pad 10) such that the absorbent layer(s) 20 terminate proximate the peripheral seal region 34. The dimensions of the absorbent layer(s) 20 can be substantially similar to those of the sanitary pad 10, however it will be appreciated that the dimensions of the absorbent layer 20 while similar, will often be slightly less than those of the overall sanitary pad 10 in order to be adequately contained therein, and desirably sealed around the edges. Desirably in one embodiment, the absorbent layer 20 is either an airlaid layer, a SAP impregnated sheet or a combination of the two. Such absorbent layer 20 may in one embodiment, be constructed of a blend of synthetic fibers in a spunlace web such as for example, a blend of PET and rayon fibers, or alternatively, a homogeneous layer of 100 percent rayon fibers, air-laid materials, or foam rubber materials.

The individual layers comprising the sanitary pad 10 can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis.

The liquid impermeable backsheet layer 18 functions to isolate absorbed fluids from the wearer's garments or bedding, and therefore desirably can comprise a variety of liquid-impervious materials. In one aspect, the liquid impermeable backsheet layer 18 may optionally comprise a material that prevents the passage of liquids but allows air and water-vapor to pass there-through. The liquid impermeable backsheet layer can comprise a single layer or multiple layers, and these one or more layers can themselves comprise similar or different materials. Suitable liquid impermeable backsheet layer 18 materials include, but are not limited to, polyolefin films, nonwovens, nonwoven laminates, and film/nonwoven laminates. The particular structure and composition of the liquid impermeable backsheet layer may be selected from various known films and/or fabrics with the particular material being selected as appropriate to provide the desired level of liquid barrier, strength, abrasion resistance, tactile properties, aesthetics (such as texture and printability) and so forth. Suitable backsheet layer 18 materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety. The liquid impermeable backsheet layer 18 may be breathable or nonbreathable, as may be desired. In one embodiment, the liquid impermeable backsheet layer is a breathable polyolefinic film having a basis weight of between about 18 gsm and 40 gsm, alternatively between about 20 gsm and 30 gsm, such as of a polyethylene film.

As noted, the absorbent articles 10 of the invention may include other additional features as are generally known in the art. Such features may include wing or tab-like features 15, which are desirably extensions of the liquid permeable topsheet layer 16 and liquid impermeable backsheet layer 18 that extend out from the opposing lateral side edges 13, 14 of the article. Such wings 15 may also be nonintegral in construction, either being attached to the topsheet layer 16 or the backsheet layer 18. The articles 10 may further be individually wrapped in a pouch, such as those which are commonly known in the art. In such an instance, such article 10 may be releasably fastened to the inside surface of such pouch for ease of article handling and eventual disposal.

Example

As an example of a sanitary pad construction in accordance with the invention, a feminine care pad may be constructed including a dual-cover topsheet layer with an encircling dual-cover topsheet configuration. The encircling dual-cover topsheet layer may consist of a 24 gsm pin-apertured nonwoven cover (TABCW) such as a PE/PP 2d bicomponent fiber, and a centrally exposed oval of a 22.5 gsm polyethylene apertured film. Subjacent to the topsheet layer may be positioned an optional first surge layer of PP/PE 2.2d bicomponent fiber in a 18 gsm TABCW. Subjacent to the first surge layer may be positioned a laminate of a 55 gsm TABCW and 85 gsm airlaid layer (total of 140 gsm) as a compressible fluid management layer in which the upper wearer-facing TABCW layer may be blue colored. Such material may include 6d PE/PP bicomponent fibers and 9 d PE/PET bicomponent fibers.

Subjacent to the compressible fluid management layer may be positioned an optional second surge layer of a 20 gsm TABCW of 2 d PE/PP bicomponent fibers. Subjacent to the optional second surge layer in the pad Z direction may be positioned an optional airlaid absorbent layer, beneath which may be positioned a fluff and SAP absorbent core layer sheet. A backsheet of 22 gsm non-breathable polyethylene film may be used to seal the peripheral edges of the topsheet layer (surrounding layer) at a peripheral seal region. Two embossed features may be used on the pad including one in an oval configuration of spaced flowers as illustrated in FIG. 1, that may be placed inward to the entire inner edge of an annular opening in the compressible fluid management layer, and one of spaced flowers that may be placed about the entire transverse and end edges of the compressible fluid management layer.

A compressible fluid management layer as described above was separately tested for compressibility/resiliency using the above described test method, with the following results.

TABLE 1

Example of Compressible Fluid Management Layer

| Material | Original thickness before compress/mm | Thickness after 2-hour compress (load removed right away)/mm | 30 minutes after compress load removal/mm |
|---|---|---|---|
| 55 gsm TABCW laminated to 85 gsmairlaid layer (Fitesa China) Total basis weight of 140 gsm | 2.48 | 2.2 | 2.45 |

As can be seen from this disclosure, a compressible fluid management layer may be used in conjunction with registered stabilizing elements, such as embossed features, so as to impart stability to the elevated compressible layer within an absorbent article. Embossing features directly join a well-like feature to subjacent layers, and desirably in one embodiment, to absorbent layer(s) beneath the well-like feature. By buttressing an elevated, but compressible layer within an article along an inner and outer compressible layer edge (at least along transverse side edges), a stable, fluid capture well-like structure can be created. Such stable well-like structure is resistant to deformation, which can improve leakage from the well-like structure and the article itself. Further, by aligning an embossed feature with such well-like structure inner and peripheral outer edges, a prominently defined contour may be created upon the wearer-facing surface of an absorbent article. Such prominent feature may be useful for the consumer in placement of the well-like feature and article beneath the specific regions of the wearer's anatomy that are most likely to be sources of body exudate. In particular, by registering an embossed feature within an annular opening of a compressible fluid management layer, but not in the compressible fluid management layer itself (and having such embossed feature align in shape with substantially the entire inner edge of the annular opening in the layer), lateral support for the compressible fluid management layer is created in areas which are traditionally exposed to significant compressive forces. By including embossed features at least adjacent the inner edge of an annular opening and also adjacent the transverse outer edge of the compressible layer, a combination of supports are created to stabilize the compressible layer. Use of embossed features both adjacent an inner edge of a compressible fluid management layer and adjacent at least transverse side outer edges of the layer also enhance the cushion-like appearance and performance of the compressible fluid management layer.

Such a compressible fluid management layer may include an extended length embodiment, such that in combination with outwardly flared embossed features along the outer transverse side edges of the compressible fluid management layer, an overnight absorbent article which uses the compressible layer may be constructed to fit comfortably within the intergluteal cleft of a wearer. Such an extended length, compressible fluid management layer therefore provides for an enhanced fluid capture, well-like feature in the crotch region of an article, as well as a rearwardly directed fluid capture feature for capturing fluid that may seep from a wearer during night-time hours.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having a longitudinal direction, a transverse direction, and a depth direction comprising: a topsheet layer, a backsheet layer, an absorbent layer between said topsheet layer and said backsheet layer, and a compressible fluid management layer between said topsheet layer and said absorbent layer, with each of said topsheet, backsheet, absorbent, and compressible fluid management layers having respective longitudinal direction, transverse direction and depth direction dimensions, said longitudinal and transverse direction dimensions defined by longitudinal direction end edges and transverse direction side edges respectively;

wherein said compressible fluid management layer has an inner edge that defines an annular opening, said annular opening extending entirely through said compressible fluid management layer depth direction dimension to form a well-like structure, said well-like structure comprising a floor positioned at a level below a top surface of said compressible fluid management layer in said depth direction, said compressible fluid management layer including a transverse dimension which is smaller than the transverse dimension of said absorbent layer; and further wherein said absorbent article further comprising a first embossed feature, said first embossed feature positioned within said topsheet layer and said absorbent layer such that said topsheet layer and said absorbent layer are held together at said floor of said well-like structure, and a second embossed feature configured at least at portions, lateral to at least said compressible fluid management layer transverse direction side edges and positioned within said topsheet layer and said absorbent layer.

2. The absorbent article of claim 1, wherein said compressible fluid management layer extends a length along the majority of the longitudinal direction of said absorbent layer.

3. The absorbent article of claim 1, wherein said compressible fluid management layer includes at least one flared longitudinal direction end.

4. The absorbent article of claim 1, wherein at least a portion of said embossed feature is positioned a lateral distance from the inner edge by between about 0.5 mm and 10 mm.

5. The absorbent article of claim 4, wherein said lateral distance is between about 1.0 mm and 5 mm.

6. The absorbent article of claim 5, wherein said lateral distance is between about 1 mm and 3 mm.

7. The absorbent article of claim 1, wherein the entirety of said first embossed feature is positioned within said annular opening.

8. The absorbent article of claim 1, wherein said first embossed feature is selected from the group consisting of a continuous embossed channel and a discontinuous series of discrete embossed shapes, wherein said inner edge has an overall shape, and further wherein the first embossed feature is configured to be of the same shape as the inner edge overall shape.

9. The absorbent article of claim 1, wherein at least a portion of said embossed feature is positioned laterally outward from the compressible fluid management layer transverse direction side edges by a distance of between about 0.5 mm and 200 mm.

10. The absorbent article of claim 9, wherein said distance is between about 1 mm and 100 mm.

11. The absorbent article of claim 10, wherein said distance is between about 1 mm and 20 mm.

12. The absorbent article of claim 9, wherein the entirety of said second embossed feature is positioned laterally outward from the compressible fluid management layer transverse direction side edges and longitudinal direction end edges.

13. The absorbent article of claim 1, wherein said second embossed feature is selected from the group consisting of a continuous embossed channel and a discontinuous series of discrete embossments.

14. The absorbent article of claim 1, wherein said compressible fluid management layer transverse direction dimension includes non-straight side edge portions along the article longitudinal direction.

15. The absorbent article of claim 1, wherein said compressible fluid management layer includes a first, forward-directed region having a forward-directed region length, and having a maximum transverse dimension width, a second middle region which includes said annular opening, and an elongated rearward-directed region of a length longer than said forward-directed region length, and having a transverse dimension width which is narrower than said first, forward-directed region maximum transverse width.

16. The absorbent article of claim 15, wherein said second embossed feature includes outwardly flared end elements, which are flared away from the compressible fluid management layer, transverse dimension side edges.

17. The absorbent article of claim 1, wherein said inner edge defining said annular opening has a shape, and said first embossed feature is of the same overall shape as said inner edge.

18. The absorbent article of claim 1, wherein said second embossed feature is discontinuous and includes at least two separated ends, and wherein said compressible fluid management layer extends beyond said at least separated ends of said second embossed feature along the article longitudinal direction.

19. The absorbent article of claim 1, wherein said absorbent article includes a vaginal placement zone, a gluteal cleft transition zone, and a coccyx zone, and further wherein said compressible fluid management layer has a length that extends into said coccyx zone.

20. The absorbent article of claim 1, wherein said compressible fluid management layer includes discrete apertures in addition to said annular opening.

21. The absorbent article of claim 1, wherein said first and second embossed features are shaped to align with the inner edge of the compressible fluid management layer and transverse dimension side edges of the compressible fluid management layer, respectively.

22. The absorbent article of claim 1, wherein said compressible fluid management layer is formed from a laminate of at least two layers.

23. The absorbent article of claim 1 wherein said compressible fluid management layer includes a thickness in the depth direction between about 1 and 20 mm.

24. The absorbent article of claim 23, wherein said thickness is between about 1.5 and 10 mm.

25. The absorbent article of claim 24, wherein said thickness is between about 2 and 5 mm.

26. The absorbent article of claim 1, wherein said topsheet layer is a dual-cover topsheet layer, having a first skin exposed topsheet layer material surrounded about all its side edges by a second skin exposed topsheet layer material, and further wherein said first skin exposed topsheet layer material includes skin exposed longitudinal and transverse edge dimensions larger than the longitudinal and transverse dimensions of said compressible fluid management layer.

27. The absorbent article of claim 1, wherein said topsheet layer is a dual-cover topsheet layer having a first skin-exposed topsheet layer material surrounded about all its skin-exposed side edges by a second skin-exposed topsheet layer material, and further wherein said first skin-exposed topsheet layer includes exposed longitudinal and transverse edge dimensions smaller than the inner edge of said annular opening.

28. An absorbent article having a longitudinal direction, a transverse direction, and a depth direction comprising: a topsheet layer, a backsheet layer, at least one subjacent layer between said topsheet layer and said backsheet layer, and a compressible fluid management layer between said topsheet layer and said at least one subjacent layer, with each of said topsheet, backsheet, at least one subjacent layer, and compressible fluid management layers having respective longitudinal direction, transverse direction and depth direction dimensions, said longitudinal and transverse direction dimensions defined by longitudinal direction end edges and transverse direction side edges respectively;

wherein said compressible fluid management layer has an inner edge that defines an annular opening, said annular opening extending entirely through said compressible fluid management layer depth direction dimension to form a well-like structure, said well-like structure comprising a floor positioned at a level below a top surface of said compressible fluid management layer in said depth direction, said compressible fluid management layer including a transverse dimension which is smaller than the transverse dimension of said at least one subjacent layer; and further wherein said absorbent article further comprising a first embossed feature positioned at least at portions, within said annular opening, and adjacent to said compressible fluid management layer inner edge, said first embossed feature positioned within said topsheet layer and said at least one subjacent layer such that said topsheet layer and said absorbent layer are held together at said floor of said well-like structure, and a second embossed feature configured at least at portions, lateral to at least said compressible fluid management layer transverse direction side edges and positioned within said topsheet layer and said at least one subjacent layer.

29. The absorbent article of claim 28, wherein said inner edge has an overall shape, and said first embossed feature is positioned entirely within said annular opening and has an overall shape that is the same overall shape as that of the inner edge.

30. The absorbent article of claim 28, wherein said second embossed feature is positioned laterally outward from, but adjacent to said transverse direction side edges and longitudinal direction end edges of the compressible fluid management layer.

31. The absorbent article of claim 28, wherein said absorbent article includes two longitudinal ends along said longitudinal direction, and said compressible fluid management layer is of a length that extends along a substantial portion of the longitudinal direction of said absorbent article, and further wherein said second embossed feature includes two separated, and outwardly flared ends at one longitudinal end of said absorbent article.

32. An absorbent article having a longitudinal direction, a transverse direction, and a depth direction comprising: a topsheet layer, a backsheet layer, at least one subjacent layer between said topsheet layer and said backsheet layer, and a compressible fluid management layer between said topsheet layer and said at least one subjacent layer, with each of said topsheet, backsheet, at least one subjacent, and compressible fluid management layers having respective longitudinal direction, transverse direction and depth direction dimensions, said longitudinal and transverse direction dimensions defined by longitudinal direction end edges and transverse direction side edges respectively;

wherein said compressible fluid management layer has an inner edge of an inner edge shape, that defines an annular opening, said annular opening extending entirely through said compressible fluid management layer depth direction dimension to form a well-like structure, said well-like structure comprising a floor positioned at a level below a top surface of said compressible fluid management layer in said depth direction, said compressible fluid management layer including a transverse dimension which is smaller than the transverse dimension of said at least one subjacent layer; and further wherein said absorbent article further comprising a first stabilizing element positioned at least at portions, within said annular opening, and adjacent to said compressible fluid management layer inner edge, said first stabilizing element positioned within said topsheet layer and said at least one subjacent layer and having the same shape as the inner edge shape, such that said topsheet layer and said absorbent layer are held together at said floor of said well-like structure, and a second stabilizing element configured at least at portions, lateral to at least said compressible fluid management layer transverse direction side edges and positioned within said topsheet layer and said at least one subjacent layer.

* * * * *